US010822583B2

(12) United States Patent
Bonito et al.

(10) Patent No.: US 10,822,583 B2
(45) Date of Patent: Nov. 3, 2020

(54) LIPID BIOSYNTHESIS AND ABIOTIC STRESS RESILIENCE IN PHOTOSYNTHETIC ORGANISMS

(71) Applicant: Board of Trustees of Michigan State University, East Lansing, MI (US)

(72) Inventors: Gregory Bonito, East Lansing, MI (US); Zhi-Yan Du, East Lansing, MI (US); Christoph Benning, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/894,457

(22) Filed: Feb. 12, 2018

(65) Prior Publication Data

US 2018/0230420 A1    Aug. 16, 2018

Related U.S. Application Data

(60) Provisional application No. 62/458,236, filed on Feb. 13, 2017.

(51) Int. Cl.
  *C12N 1/12*  (2006.01)
  *C12N 1/14*  (2006.01)
  *C12R 1/89*  (2006.01)
  *C12R 1/645* (2006.01)

(52) U.S. Cl.
  CPC .............. *C12N 1/12* (2013.01); *C12N 1/14* (2013.01); *C12R 1/645* (2013.01); *C12R 1/89* (2013.01); *C12N 2500/34* (2013.01)

(58) Field of Classification Search
  CPC ...................................................... C12N 1/12
  See application file for complete search history.

(56) References Cited

U.S. PATENT DOCUMENTS

| | | |
|---|---|---|
| 5,258,300 A | 11/1993 | Glassman et al. |
| 2008/0264858 A1 | 10/2008 | Stamets |
| 2010/0255550 A1 | 10/2010 | Benning et al. |
| 2018/0346954 A1 | 12/2018 | Bonito et al. |

OTHER PUBLICATIONS

Ahmadjian V, Science, 1966, 151:199-201.*
Gorbushina et al. Mycol. Res., 2005, 109(11):1288-1296.*
Vieler et al. PLOS Genetics, 2012, 8(11):1-25.*
Spatafora et al. Mycologia, 2016, 108(5):1028-1046.*
Behera et al. Food Technol. Biotechnol., 2009, 47(1):7-12.*
Atsatt, P. R., "Are vascular plants "inside-out" lichens?", Ecology. 69(1), (1988), 17-23.
Bevan, M., "Binary Agrobacterium vectors for plant transformation.", Nucleic Acids Research, 12(22), (1984), 8711-8721.
Bonfante, P., et al., "Mechanisms underlying beneficial plant-fungus interactions in mycorrhizal symbiosis", Nat. Commun. 1:48, (2010), 1-11.
Bonito, G., et al., "Isolating a functionally relevant guild of fungi from the root microbiome of Populus", Fungal Ecol. 22, (Aug. 2016), 35-42.
Brenner, K., et al., "Engineering microbial consortia: a new frontier in synthetic biology", Trends Biotechnol. 26(9), (2008), 483-489.
Chen, H. L., et al., "Conditional production of a functional fish growth hormone in the transgenic line of Nannochloropsis oculata (Eustigmatophyceae)", J. Phycol., 44(3), (2008), 768-776.
Delaux, P.-M., et al., "Algal ancestor of land plants was preadapted for symbiosis", Proc. Natl. Acad. Sci. USA. 112(43), (2015), 13390-13395.
Field, K. J., et al., "Functional analysis of liverworts in dual symbiosis with Glomeromycota and Mucoromycotina fungi under a simulated Palaeozoic CO2 decline", ISME J. 10, (2015), 1514-1526.
Field, K. J., et al., "Symbiotic options for the conquest of land", Trends Ecol. Evol. 30(8), Pressel, (2015), 477-486.
Hom, E. F. Y., et al., "Niche engineering demonstrates a latent capacity for fungal-algal mutualism", Science, 345(6192), (2014), 94-98.
Jefferson, R. A., "Assaying Chimeric Genes in Plants: The GUS Gene Fusion System", Plant Mol. Biol. Rep., 5(4), (1987), 387-405.
Little, A. F., et al., "Flexibility in Algal Endosymbioses Shapes Growth in Reef Corals", Science. 304(5676), (2004), 1492-1494.
Mollenhauer, D., "Studies on initiation and development of the partner association in Geosiphon pyriforme (Kütz.) v. Wettstein, a unique endocytobiotic system of a fungus (Glomales) and the cyanobacterium Nostoc punctiforme (Kütz.) Hariot", Protoplasma. 193(1-4), (1996), 3-9.
Okamoto, N., et al., "A secondary symbiosis in progress?", Science, 310(5746), (2005), p. 287.
Partida-Martinez, I. P., et al., "A Gene Cluster Encoding Rhizoxin Biosynthesis in "Burkholderia Rhizoxina", the Bacterial Endosymbiont of the Fungus Rhizopus microsporus", Chembiochem., 8(1), (2007), 41-45.
Poliner, E., et al., "Transcriptional coordination of physiological responses in Nannochloropsis oceanicaCCMP1779 under light/dark cycles", The Plant Journal, 83(6), (2015), 1097-1113.
Redecker, D., et al., "Glomalean fungi from the Ordovician", Science. 289(5486), (2000), 1920-1921.
Scholz, M. J., et al., "Ultrastructure and Composition of the Nannochloropsis gaditana Cell Wall", Eukaryot. Cell. 13, (2014), 1450-1464.
Service, R. F., et al., "Algae's Second Try", Science, 333(6047), (2011), 1238-1239.
Simon, J., et al., "Self-supporting artificial system of the green alga Chlamydomonas reinhardtii and the ascomycetous fungus Alternaria infectoria", Symbiosis, 71(3), (Mar. 2017), 199-209.

(Continued)

*Primary Examiner* — Bin Shen

(74) *Attorney, Agent, or Firm* — Schwegman Lundberg & Woessner, P.A.

(57) ABSTRACT

This application describes consortium between fungi and algae, where the algae are incorporated within hyphae of the fungi. The consortium is robust. The fungi and algae can symbiotically provide nutrients to each other, and are tolerant of environmental stresses.

12 Claims, 20 Drawing Sheets
(15 of 20 Drawing Sheet(s) Filed in Color)
Specification includes a Sequence Listing.

(56) References Cited

OTHER PUBLICATIONS

Spatafora, J. W., et al., "A phylum-level phylogenetic classification of zygomycete fungi based on genome-scale data", Mycologia, 108(5), (2016), 1028-1046.

Thillet, J., et al., "Site-directed Mutagenesis of Mouse Dihydrofolate Reductase. Mutants with increased resistance to methotrexate and trimethoprim", The Journal of Biological Chemistry, 263(25), (Sep. 5, 1988), 12500-12508.

Tisserant, E., et al., "Genome of an arbuscular mycorrhizal fungus provides insight into the oldest plant symbiosis", Proc. Natl. Acad. Sci. USA. 110(50), (2013), 20117-20122 (8 pgs.).

Tsai, C.-H., et al., "The protein Compromised Hydrolysis of Triacylglycerols 7 (CHT7) acts as a repressor of cellular quiescence in Chlamydomonas", Proc. Natl. Acad. Sci. USA, 111, (2014), 15833-15838.

Velichkov, A. D., et al., "A simple procedure for dissolving fungal cell wall preparations for the analysis of neutral sugars", World J. Microbiol. Biotechnol., 8(5), (1992), 527-528.

Vieler, A., et al., "Genome, Functional Gene Annotation, and Nuclear Transformation of the Heterokont Oleaginous Alga Nannochloropsis oceanica CCMP1779", PLoS Genet. 8(11): e1003064, (2012), 1-25.

Wodniok, S., et al., "Origin of land plants: do conjugating green algae hold the key?", BMC Evol. Biol. 11:104, (2011), 10 pgs.

Zienkiewicz, K., et al., "Nannochloropsis, a rich source of diacylglycerol acyltransferases for engineering of triacylglycerol content in different hosts", Biotechnol Biofuels, 10:8, (2017), 20 pgs.

An, G., "[17] Binary ti vectors for plant transformation and promoter analysis", Method in Enzymology, vol. 153, (1987), 292-305.

Georgianna, D. R., et al., "Exploiting diversity and synthetic biology for the production of algal biofuels", Nature 2012, 488(7411), (2012), 329-335.

Jia, J., et al., "Molecular mechanisms for photosynthetic carbon partitioning into storage neutral lipids in Nannochioropsis oceanica under nitroaen-depletion conditions", Algal Research, vol. 7, (Jan. 2015), 66-77.

Murakami, T., et al., "The Biaiaphos Biosynthetic Genes of *Streptomyces hygroscopicus*: Molecular Cloning and Characterization of the Gene Cluster", Mol. Gen. Genet., 205, (1986), 42-50.

"U.S. Appl. No. 16/058,632, Restriction Requirement dated Mar. 3, 2020", 5 pgs.

"U.S. Appl. No. 16/058,632, Response filed May 27, 2020 to Restriction Requirement dated Mar. 3, 2020", 7 pgs.

"International Application Serial No. PCT/US2020/020412, International Search Report dated Jun. 15, 2020", 3 pgs.

"International Application Serial No. PCT/US2020/020412, Written Opinion dated Jun. 15, 2020", 7 pgs.

\* cited by examiner

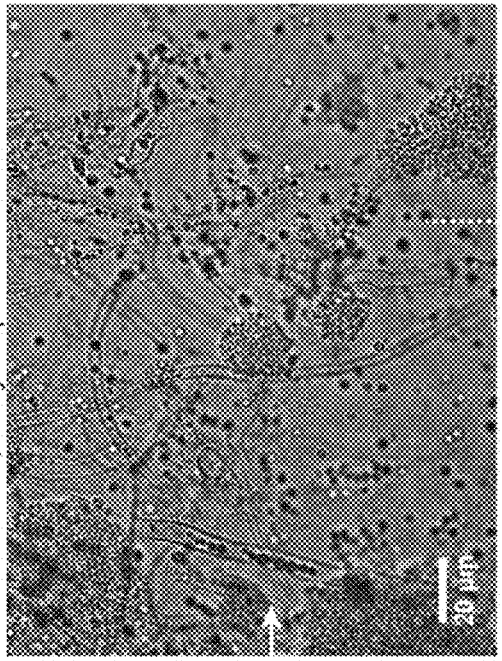
FIG. 4I-2
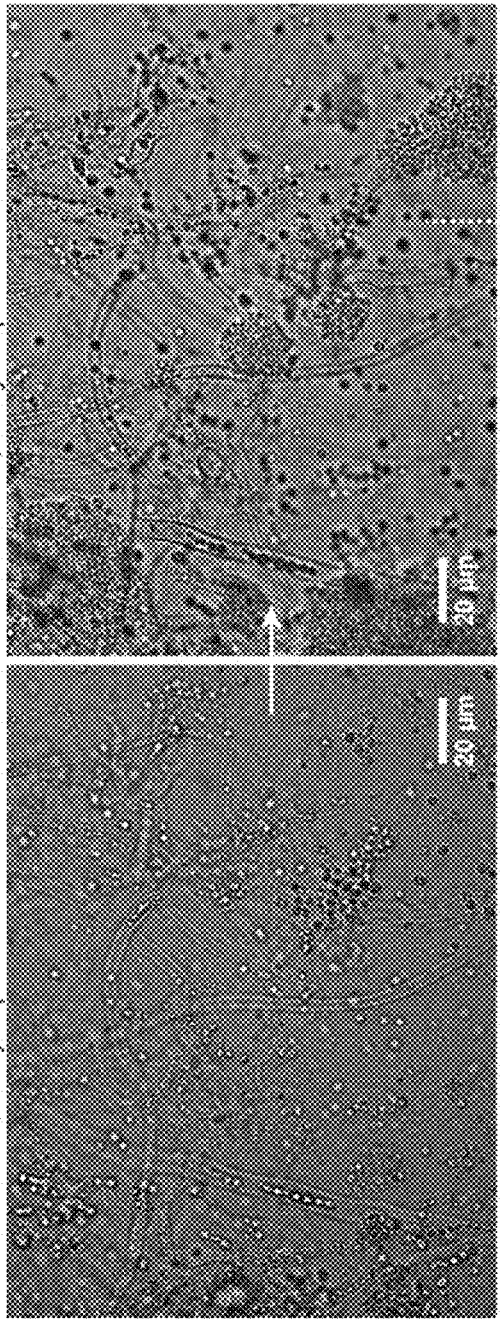
FIG. 4I-1
FIG. 4I-4
FIG. 4I-3

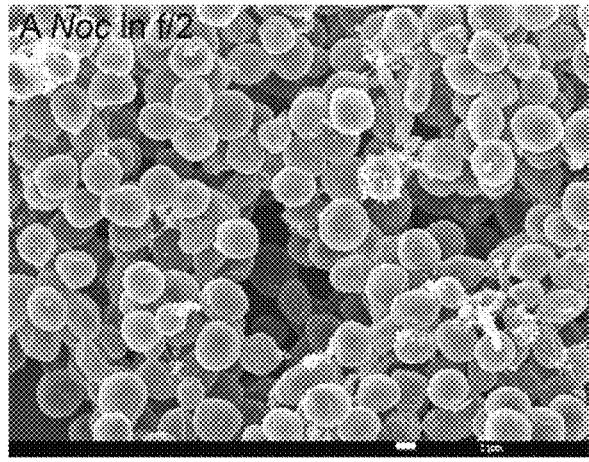
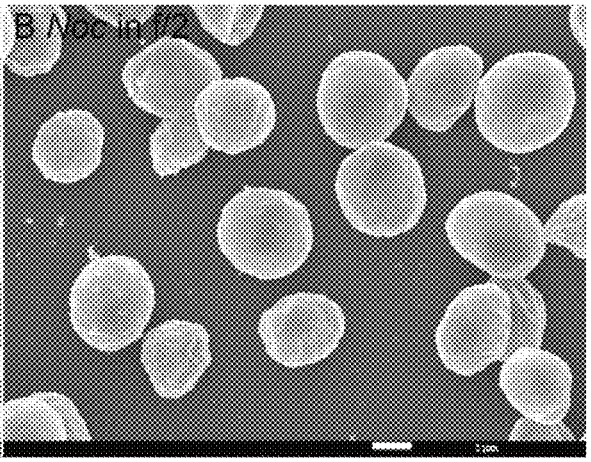
FIG. 5A     FIG. 5B
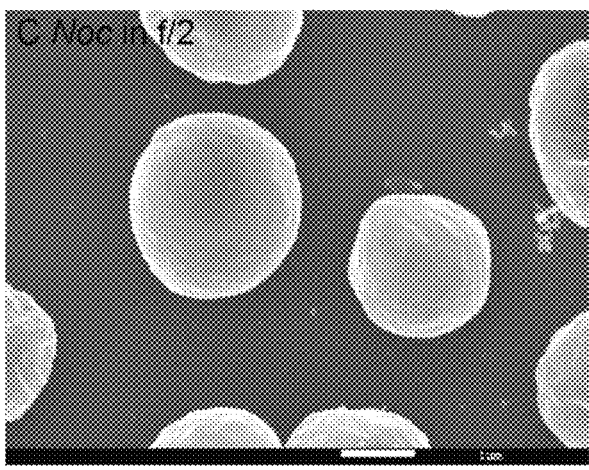
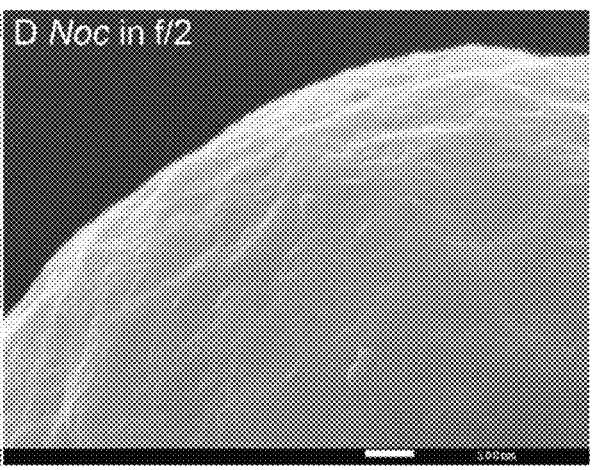
FIG. 5C     FIG. 5D

LIPID BIOSYNTHESIS AND ABIOTIC STRESS RESILIENCE IN PHOTOSYNTHETIC ORGANISMS

This application claims benefit of priority to the filing date of U.S. Provisional Application Ser. No. 62/458,236, filed Feb. 13, 2017, the contents of which are specifically incorporated herein by reference in their entirety.

BACKGROUND OF THE INVENTION

Microbes have been used for many manufacturing purposes, including for energy production and the production of useful materials. For example, market prices for energy and fuels have been comparatively low but easily accessible petroleum and natural gas deposits have been depleted. In addition, emerging economies are growing, and environmental concerns are also growing. Significant restructuring or replacement of a portion of fossil fuels may be needed, for example, by renewable energy technologies such as biofuels. Currently, the largest volume of biofuels today is in the form of bioethanol for spark-ignition engines, with a smaller amount in the form of biodiesel for compression-ignition engines. Both bioethanol and biodiesel are produced primarily from terrestrial plant material. However, it is not optimal in the long term to produce fuels using food crops since food crops require premium land, abundant water, and large inputs of energy in the form of agricultural machinery and fertilizer. Thus, it would be advantageous to produce biofuels from alternative sources.

SUMMARY

Described herein are methods for making living fungal mycelia that have incorporated photosynthetically active algal cells within their hyphae. The consortia formed by fungi and algae are robust, and can supply each other with nutrients. For example, the photosynthetic apparatus of algae can supply both the algae and the fungus with useful carbon-based nutrients. As illustrated herein, methods of making such fungal/algal consortia are simple and efficient. Hence, the costs of making, growing, and maintaining fungal/algal consortia are low. Such fungal/algal consortia are therefore useful for making a variety of compounds and materials, including oils, biofuels, and biomass.

One aspect of the invention is a consortium that includes at least one viable fungus and at least one viable algae within hyphae of the fungus. Such consortia are not products of nature. For example, many tested interactions between fungi and algae failed to form consortia.

The conditions describe herein facilitated formation of consortia. Another aspect is a method that includes incubating at least one fungus and at least one algae cell until at least one algae cell is incorporated into hyphae of the fungus, to thereby form a consortium of the at least one fungus and the at least one algae cell.

DESCRIPTION OF THE FIGURES

The patent or application file contains at least one drawing executed in color. Copies of this patent or patent application publication with color drawing(s) will be provided by the Office upon request and payment of the necessary fee.

FIGS. 2A-2H illustrate carbon exchange between *N. oceanica* and *M. elongata* AG77. FIG. 2A includes FIGS. 2A-1 and 2A-2, which illustrate carbon (C) transfer from [$^{14}$C]sodium bicarbonate (NaHCO$_3$)-labeled *N. oceanica* (Noc) cells to *M. elongata* AG77 (FIG. 2A-1) or from [$^{14}$C]glucose-labeled AG77 to Noc cells (FIG. 2A-2) after 7-day co-culture in flasks with physical contact between the *N. oceanica* and *M. elongata* AG77. Radioactivity of $^{14}$C was measured with a scintillation counter (dpm, radioactive disintegrations per minute) and then normalized to the dry weight of samples (dpm/mg biomass). Free Noc refers to unbound Noc cells in supernatant. Attached refers to Noc cells separated from AG77-Noc aggregates. FAAs refers to free amino acids. The "soluble compounds" refers to compounds in the supernatant after acetone precipitation of proteins extracted by SDS buffer. Data are presented in the average of three biological repeats with standard deviation (Means±SD, n=3). FIG. 2B includes FIGS. 2B-1 and 2B-2, which illustrate radioactive $^{14}$C transfer between Noc and AG77 without physical contact. Algae and fungi were incubated in cell-culture plates with filter-bottom inserts (pore size of 0.4 μm) which separate Noc cells and AG77 mycelia from each other but allow metabolic exchange during co-culture. Error bars indicate SD (n=3). Radioactive carbon (C) transfer was measured from [$^{14}$C]sodium bicarbonate (NaHCO$_3$)-labeled *N. oceanica* (Noc) cells to *M. elongata* AG77 (FIG. 2B-1) or from [$^{14}$C]glucose-labeled AG77 to Noc cells (FIG. 2B-2). FIG. 2C illustrates the relative abundance of $^{14}$C radioactivity in AG77 recipient cells compared to $^{14}$C-labeled Noc donor cells after 7-day co-culture (total AG77 dpm/total $^{14}$C-Noc dpm). FIG. 2D illustrates the relative abundance of $^{14}$C radioactivity in Noc recipient cells compared to $^{14}$C-labeled AG77 donor cells after 7-day co-culture (total Noc dpm/total $^{14}$C-AG77 dpm). Physical contact refers to living $^{14}$C-labeled cells added to unlabeled cells for co-cultivation in flasks. No contact refers to samples grown separately in plates with inserts. Heat-killed $^{14}$C-cells, heat-killed $^{14}$C-labeled Noc or heat-killed AG77 were killed by heat treatment at 65° C. for 15 min before the addition to unlabeled cells in flasks. Free refers to unbound Noc cells in supernatant. Att refers to Noc cells attached to AG77. Total refers to Noc cells grown separately with AG77 in plates and inserts. Error bars indicate SD (n=3). FIGS. 2E-2H further illustrate $^{14}$C exchange between *N. oceanica* and *M. elongata* AG77 without physical contact. FIG. 2E illustrates co-culture of *N. oceanica* (Noc) and *M. elongata* AG77 in 6-well plates with filter-bottom inserts (i.e., without physical contact). FIG. 2F illustrates co-culture of *N. oceanica* (Noc) and *M. elongata* AG77 in 6-well plates with filter-bottom inserts (i.e., without physical contact), and after 7-day co-culture, the inserts were moved to the adjacent empty wells (bottom) for harvesting samples. There is no cross contamination observed between Noc and AG77 samples as suggested by the images. FIG. 2G shows a side-view schematic diagram of alga-fungus co-culture (e.g., as illustrated in FIG. 2E) and sample harvesting (e.g., as illustrated in FIG. 2F) with an insert and plate. The hydrophilic polytetrafluoroethylene filter (pore size of 0.4 µm) at the bottom of the inserts separates Noc and AG77 during co-culture but allows metabolic exchange between the plate well and insert. [$^{14}$C]sodium bicarbonate (NaHCO$_3$)-labeled Noc cells were grown in the plate well or insert while recipient AG77 was grown in the insert or plate well, respectively. Similar incubation conditions were used for [$^{14}$C]glucose- or [$^{14}$C]sodium acetate-labeled AG77 and recipient Noc. FIG. 2H graphically illustrates $^{14}$C transfer from [$^{14}$C]sodium acetate-labeled AG77 to recipient Noc. $^{14}$C radioactivity (dpm, radioactive disintegrations per minute) was normalized to the dry weight (dpm/mg). FAAs, free amino acids; soluble compounds, supernatant after acetone precipitation of SDS-protein extraction. Error bars indicate SD (n=3).

FIG. 3A illustrates nitrogen (N) exchange between *N. oceanica* (Noc) and *M. elongata* AG77 as examined by $^{15}$N-labeling experiments. [$^{15}$N] potassium nitrate-labeled Noc cells or [$^{15}$N]ammonium chloride-labeled AG77 were added to unlabeled AG77 or Noc cells, respectively, for 7-days co-culture in flasks (physical contact) or for 7-days cell culture in plates with inserts (no physical contact). Algae and fungi were separated and weighed (dry biomass) after the co-culture, and their isotopic composition ($δ^{15}$N, ratio of stable isotopes $^{15}$N/$^{14}$N) and N content (% N) were determined using an elemental analyzer interfaced to an Elementar Isoprime mass spectrometer following standard protocols. The N uptake rate of $^{15}$N-Noc-derived N ($^{15}$N) by AG77 from and that of $^{15}$N-AG77-derived N by Noc cells ($^{15}$N) were calculated based on the Atom % $^{15}$N [$^{15}$N/($^{15}$N+$^{14}$N)100%], % N and biomass. C, chloroplast; N, nucleus; Nu, nucleolus; M, mitochondrion; V, vacuole; L, lipid droplet. Values are the average of three biological repeats. FIGS. 3B-3D illustrate viabilities of the *N. oceanica* (Noc) and *M. elongata* AG77 under various culture conditions. FIG. 3B shows images illustrating viability assays of Noc cells under nitrogen deprivation (—N). FIG. 3C shows images illustrating viability assays of Noc co-cultured with AG77 under nitrogen deprivation (—N). For FIGS. 3A and 3B, dead Noc cells were indicated by SYTOX Green staining (green fluorescence), while red colors indicate Noc chlorophyll fluorescence. FIG. 3D graphically illustrates that the viability of nutrient-deprived Noc cells increased when co-cultured with *M. elongata* AG77 or NVP64. The abbreviation —C indicates carbon deprivation. Results were calculated from 1,000 to 5,000 cells of five biological repeats with ImageJ software. Asterisks indicate significant differences compared to the Noc control by Student's t test (* P<0.05, ** P<0.01; Means±SD, n=5). FIG. 3E illustrates the total organic carbon (C) measured in the buffer of 18-day fungal cultures of *M. elongata* AG77 and NVP64 compared to the f/2 medium control (f/2 con). FIG. 3F graphically illustrates the dissolved nitrogen (N) measured in the buffer of 18-day fungal cultures of *M. elongata* AG77 and NVP64 compared to the f/2 medium control (f/2 con). Fungal cells were removed by 0.22 micron filters. Means±SD, n=4. * P<0.05, ** P<0.01. FIG. 3G-3H further illustrate nitrogen (N) exchange between *N. oceanica* and *M. elongata* AG77 as examined by $^{15}$N-labeling experiments. FIG. 3G graphically illustrates nitrogen uptake by *M. elongata* AG77 cells after [$^{15}$N]potassium nitrate-labeled Noc cells were added to unlabeled AG77 cells. FIG. 3H graphically illustrates nitrogen uptake by *N. oceanica* cells after [$^{15}$N]ammonium chloride-labeled AG77 (2.7%, Atom % $^{15}$N) were added to unlabeled Noc cells. The results in FIG. 2G were generated by addition of [$^{15}$N]potassium nitrate-labeled Noc cells [7.1%, Atom % $^{15}$N, $^{15}$N/($^{15}$N+$^{14}$N)100%] to unlabeled AG77 for 7-day co-culture in flasks (physical contact, top) or cell-culture plates with inserts (no physical contact, bottom). Similarly, the results in FIG. 3H were generated by addition of [$^{15}$N]ammonium chloride-labeled AG77 (2.7%, Atom % $^{15}$N) to unlabeled Noc cells for 7-day co-culture in flasks (physical contact, top) or cell-culture plates with inserts (no physical contact, bottom). Algae and fungi were separated and weighed (dry biomass) after the co-culture, and their isotopic composition ($δ^{15}$N, ratio of stable isotopes $^{15}$N/$^{14}$N) and N content (% N) were determined using an elemental analyzer interfaced to an Elementar Isoprime mass spectrometer following standard protocols. For FIG. 3G, the nitrogen uptake rates (µmol N/mg biomass/d) of Noc from the media (medium-N, isotope dilution) and that of AG77 from $^{15}$N-Noc-derived N ($^{15}$N) were calculated based on the Atom % $^{15}$N, % N and biomass. Error bars indicate SD (n=3). Similar analyses were carried out to obtain the results in FIG. 3H where [$^{15}$N]ammonium chloride-labeled AG77 (2.7%, Atom % $^{15}$N) and unlabeled Noc cells were incubated to calculate the uptake rate of medium-N by AG77 and that of $^{15}$N-AG77-derived N ($^{15}$N) by Noc cells. Error bars indicate SD (n=3). FIGS. 3I-3J illustrate that various fungi from diverse clades exhibit intensive interaction with *N. oceanica*. FIG. 3I schematically illustrates the phylogeny of plant root-associated fungal isolates that were used for co-culture bioassay experiments. A phylogenetically diverse panel of basidiomycete, ascomycete and zygomycete fungi were tested. FIG. 3J illustrates co-culture of *N. oceanica* cells with different fungi and *Saccharomyces cerevisiae* in flasks containing f/2 media for 6 days. *N. oceanica*, algal culture control; the others, *N. oceanica* incubated with respective fungi or *S. cerevisiae*.

FIGS. 4A-4I (where FIG. 4I includes FIG. 4I-1 to 4I-4) illustrate intracellular localization of long-term co-cultured *N. oceanica* within *M. elongata* AG77 hyphae. FIGS. 4A-4C are transmission electron microscope (TEM) images of increasing magnification showing a cross section of AG77 mycelium containing a cluster of dividing Noc cells. AG77 and Noc were co-cultured for ~one month. Red arrow heads indicate same position. M, mycelium; Mw, *Mortierella* cell wall; Nw, Noc cell wall; C, chloroplast; Cy, cytoplasm; V, vacuole. FIG. 4A shows an image of *N. oceanica* within *M. elongata* AG77 hyphae. FIG. 4B shows an enlarged imaged of the boxed area shown in FIG. 4A. FIG. 4C shows a further enlargement of a portion of the image shown in FIG. 4B. FIGS. 4D-4H shows differential interference contrast (DIC) images of AG77 "green hyphae" with *N. oceanica* (Noc) cells inside. Red arrow heads indicate putative dividing Noc cells. FIG. 4D shows *N. oceanica* (Noc) cells inside *M. elongata* AG77 hyphae after co-culture for about one month. FIG. 4E also shows Noc cells inside *M. elongata* AG77 hyphae after co-culture for about one month. FIG. 4F shows Noc cells inside *M. elongata* AG77 hyphae after co-culture for about two months. FIG. 4G also shows Noc cells inside *M. elongata* AG77 hyphae after co-culture for about two months. FIG. 4H also shows Noc cells inside *M. elongata* AG77 hyphae after co-culture for about two months. FIG. 4I-1 to 4I-4 illustrate the origin of endosymbiosis of *N. oceanica* within *M. elongata* AG77. FIG. 4I-1 shows a differential interference contrast (DIC) micrograph of co-cultured *N. oceanica* (Noc) and *M. elongata* AG77 using a Leica DMi8 DIC microscope. After 35-day co-culture in flasks, AG77-Noc aggregates were transferred to 35 mm-microwell dish (glass top and bottom, MatTek) containing soft solid media (f/2 media supplemented with 0.25% low gelling temperature agarose and 10% PDB) to investigate the establishment of the Noc endosymbiosis in AG77. The red arrow head indicates a hypha coated by Noc cells around the hyphal tip. FIG. 4I-2 to 4I-4 show a differential interference contrast (DIC) micrograph of co-cultured Noc and *M. elongata* AG77 after three days of incubation in soft solid media, the same group of Noc and AG77 cells formed a "green hypha" (with Noc cells inside) as indicated by the red arrow head. Noc cells surrounding the hypha kept growing and dividing and formed a lollipop-like structure because of the solid media, which is not observed in liquid alga-fungus co-culture. In the enlargement of the lollipop region, the cyan arrow head points to Noc cells inside the fungal hypha. FIG. 4I-2 shows a field of *N. oceanica* (Noc) and *M. elongata* AG77. FIG. 4I-3 shows an enlargement of a portion of the image shown in FIG. 4I-4. FIG. 4I-4 shows an enlargement of a portion of the image shown in FIG. 4I-2.

FIG. 5A-5H illustrates physical interaction between algal *N. oceanica* and fungal *M. elongata* cells led to the degradation of the outer layer of *N. oceanica* algal cell wall. FIG. 5A shows lower magnification images of *N. oceanica* (Noc) cells incubated alone in f/2 medium (bar=1 micron). FIG. 5B shows somewhat higher magnification images of Noc cells incubated alone in f/2 medium (bar=1 micron). FIG. 5C shows even higher magnification images of Noc cells incubated alone in f/2 medium (bar=1 micron). FIG. 5D shows an image of an Noc cell wall after incubation of the Noc cell alone in f/2 medium (bar=100 nm). As illustrated, the Noc cells shown in FIG. 5A-5D have a smooth surface. FIG. 5E shows an image of Noc cells attached to *M. elongata* AG77 (AG77) hyphae in a co-culture (bar=10 microns), illustrating that the outer layer of the Noc algal cell walls is not as intact as that of the Noc controls shown in FIG. 5A-5D. FIG. 5F shows an expanded image of Noc cells attached to *M. elongata* AG77 (AG77) hyphae in a co-culture (bar=1 micron), illustrating that the outer layer of the Noc algal cell walls is not as intact as that of the Noc controls shown in FIG. 5A-5D. FIG. 5G further illustrates the structure of *N. oceanica* (Noc) cells without physical interaction with *M. elongata* AG77 (AG77) (bar=1 micron) when using a 6-well culture plate and membrane insert (pore size of 0.4 μm) that separates the Noc and AG77 cells but allows metabolic exchange between the partners. FIG. 5H shows an expanded view of one *N. oceanica* (Noc) (bar=1 micron) cell incubated without physical interaction with *M. elongata* AG77 (AG77) by using a 6-well culture plate and membrane insert (pore size of 0.4 μm) that separates the Noc and AG77 cells but allows metabolic exchange between the partners. As shown in FIG. 5G-5H, the Noc algal cells have intact cell walls, for example in their outer layer, where in contrast, the outer layer is defective when the Noc-algal cells form a consortium with the *M. elongata* AG77 (AG77) hyphae (compare FIGS. 5E-5F with FIGS. 5G-5H).

DETAILED DESCRIPTION

Figure 1:
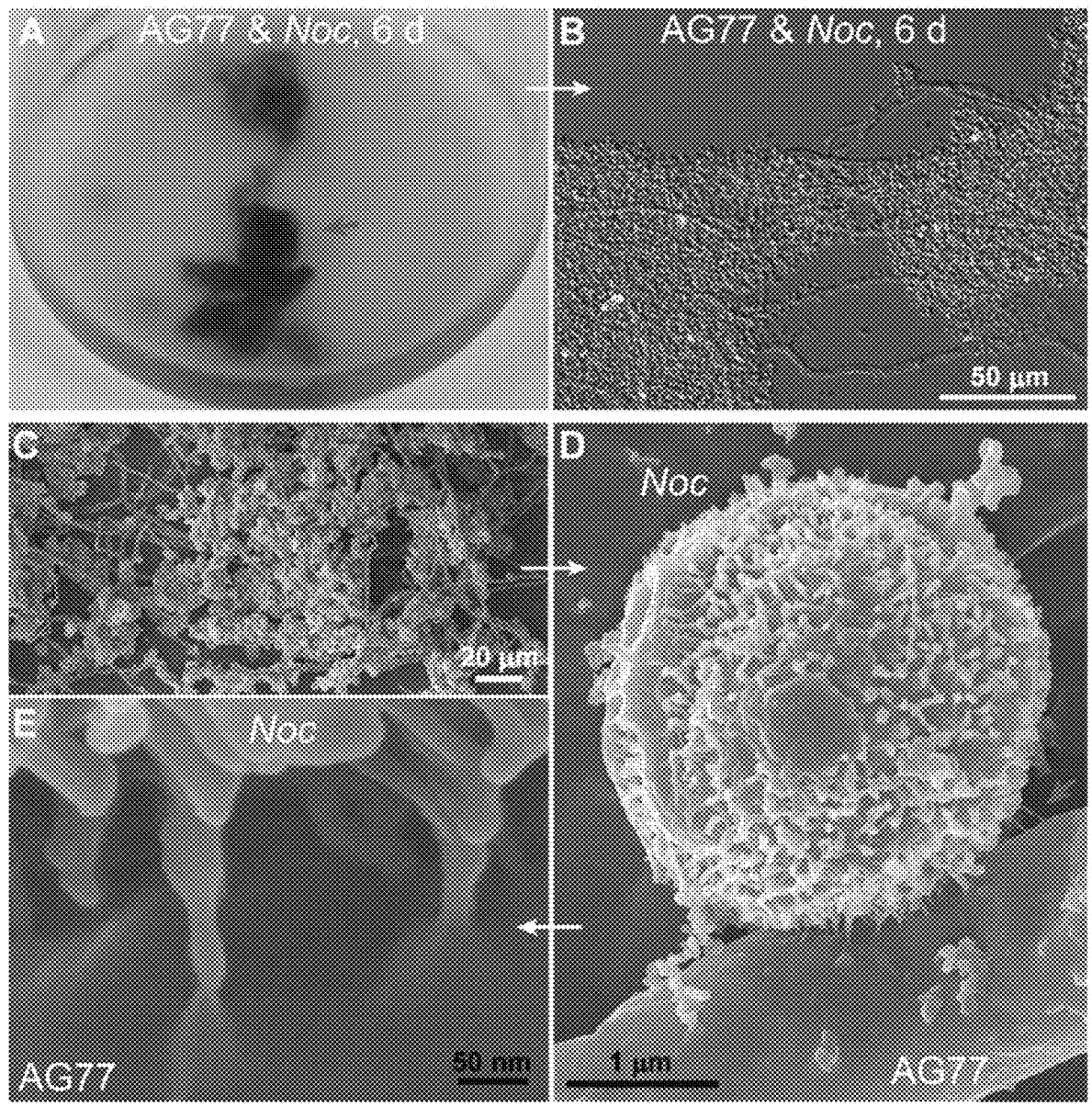
FIG. 1 illustrates interaction between the soil fungus *Mortierella elongata* and the marine algae *Nannochloropsis oceanica*. Panel A shows co-cultivation of *M. elongata* AG77 and *N. oceanica* (Noc) in flasks for 6 days. Green tissues indicated by the red arrow head are aggregates formed by AG77 mycelia and attached Noc cells. Panel B shows differential interference contrast micrographs of the green tissues shown in panel A. A large number of Noc cells were captured by AG77 mycelia. Panels C to E show images of alga-fungus aggregates by scanning electron microscopy. Panel C illustrates that Noc cells stick to the fungal mycelia after 6-d co-culture. Panel D shows a Noc cell adhering tightly to a hypha by the outer extensions of cell wall as indicated with red arrows. Panel E illustrates irregular tube-like extensions of Noc cell wall attached to the surface of fungal cell wall.

Described herein are viable fungi having viable algae within their fungi hyphae. In other words, the fungi with internalized algae form can form a consortium where, for example, the internalized algae may depend on the host fungus for nitrogen and other nutrients, while the algae can provide carbon-based nutrients and other metabolites that can be generated by algal photosynthesis. Compositions of such a consortia of fungi with viable algae within the fungi hyphae, as well as methods of making and using such consortia and compositions are also described herein.

The algae employed can include a wide variety of algae. Examples include diatoms (bacillariophytes), green algae (chlorophytes), blue-green algae (cyanophytes), and golden-brown algae (chrysophytes). In addition, a fifth group known as haptophytes may be used. Specific non-limiting examples of bacillariophytes capable of lipid production include the genera *Amphipleura, Amphora, Chaetoceros, Cyclotella, Cymbella, Fragilaria, Hantzschia, Navicula, Nitzschia, Phaeodactylum*, and *Thalassiosira*. Specific non-limiting examples of chlorophytes capable of lipid production include *Ankistrodesmus, Botryococcus, Chlorella, Chlorococcum, Dunaliella, Monoraphidium, Oocystis, Scenedesmus*, and *Tetraselmis*. In one aspect, the chlorophytes can be *Chlorella* or *Dunaliella*. Specific non-limiting examples of cyanophytes capable of lipid production include *Oscillatoria* and *Synechococcus*. A specific example of chrysophytes capable of lipid production includes *Boekelovia*. Specific non-limiting examples of haptophytes include *Isochrysis* and *Pleurochrysis*. In some cases, an alkenone-producing alga, for example a species of the *Isochrysis* family which includes, but not limited to, *Isochrysis galbana, Isochrysis* sp. T-Iso, and *Isochrysis* sp. C-Iso can be employed. Other examples of alkenone-producing algae include *Emiliania huxleyi* and *Gephyrocapsa oceanica*. In some cases, the algae is not a cyanobacterium. For example, the algae may not, in some cases, be *Nostoc punctiforme*.

Examples of algae can be species of *Amphipleura, Amphora, Aquamortierella, Chaetoceros, Charophyceae, Chlorodendrophyceae, Chlorokybophyceae, Chlorophyceae, Coleochaetophyceae, Cyclotella, Cymbella, Dissophora, Embryophytes, Endogaceae, Fragilaria, Gamsiella, Hantzschia, Klebsormidiophyceae, Lobosporangium, Mamiellophyceae, Mesostigmatophyceae, Modicella, Mortierella, Mucor, Navicula, Nephroselmidophyceae, Nitzschia, Palmophyllales, Prasinococcales, Prasinophytes, Pedinophyceae, Phaeodactylum, Pyramimonadales, Pycnoccaceae, Pythium, Phytophthora, Phytopythium, Rhizopus, Thalassiosira, Trebouxiophyceae, Ulvophyceae, Zygnematophyceae*, or a combination thereof.

In some cases, the algae is a photosynthetic algae. For example, the algae can be a strain of *Nannochloropsis oceanica*, for example *Nannochloropsis oceanica* CCMP1779.

A variety of fungi can be employed in the formation of consortia with algae. In some cases, the fungus can be a basidiomycete, ascomycete, or zygomycete. For example, one or more fungi can be a member of a genus such as: *Aspergillus, Blakeslea, Botrytis, Candida, Cercospora, Cryptococcus, Cunninghamella, Fusarium (Gibberella), Kluyveromyces, Lipomyces, Morchella, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phqffia)*, or *Yarrowia*. For example, the fungus can be a species such as: *Aspergillus terreus, Aspergillus nidulans, Aspergillus niger, Atractiella* PM1152, *Blakeslea trispora, Botrytis cinerea, Candida japonica, Candida pulcherrima, Candida revkaufi, Candida tropicalis, Candida utilis, Cercospora nicotianae, Clavulina* PM1390, *Cryptococcus curvatus, Cunninghamella echinulata, Cunninghamella elegans, Flagelloscypha* PM1526, *Fusarium fujikuroi (Gibberella zeae), Grifola frondosa* GMNB41, *Kluyveromyces lactis, Lecythophora* PM1546, *Leptodontidium* PM1413, *Lachnum* PM1789, *Lipomyces starkeyi, Lipomyces lipoferus, Mortierella alpina, Mor-* tierella elongata AG77, Mortierella gamsii GBAus22, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Umbelopsis PMI120, Xanthophyllomyces dendrorhous (Phqffia rhodozyma), Yarrowia lipolytica, or a combination thereof. In some cases, the fungus is not Geosiphon pyriformis.

In some cases, the fungus employed is a multi-celled fungi. For example, the fungus employed can have tissues and/or structures such as hyphae. Many fungi is made up of fine, branching, usually colorless threads called hyphae. Each fungus can have vast numbers of these hyphae, all intertwining to make up a tangled web called the mycelium. The mycelium is generally too fine to be seen by the naked eye, except where the hyphae are very closely packed together.

As illustrated herein, algae can reside and grow within fungal hyphae. The algae can also undergo photosynthesis within the fungi hyphae. In some cases the location of the algae is not within a fungal "bladder" and does not form a multinucleate bladder within the fungi, or a multinucleate bladder within fungal hyphae.

However, in some cases the fungus need not be a multi-celled fungus. For example, the fungus can be a one-celled organism such as a yeast.

In some cases, the fungus can be one or more of Mortierella elongata, Mortierella elongata AG77, Mortierella gamsii, Mortierella gamsii GBAus22, Umbelopsis sp., Umbelopsis PMI120, Lecythophora sp., Lecythophora PMI546, Leptodontidium sp., Leptodontidium PMI413, Lachnum sp., Lachnum PMI789, Morchella sp., Saccharomyces cerevisiae, Atractiella sp., Atractiella PMI152, Clavulina, Clavulina PMI390, Grifola frondosa, Grifola frondosa GMNB41, Flagelloscypha sp., Flagelloscypha PMI526, and combinations thereof.

Culture Media

Media for forming fungal/algal consortia can be a simple medium, especially when photosynthetic algae are employed because the algae can supply the fungi as well as the algae cells with carbon-based nutrients. Complex carbon nutrients may therefore not be needed, especially when the fungal/algal consortia are formed and the consortia are exposed to light. However, when initially preparing a consortium between one or more fungal species and one or more algae species, the fungi and algae can be cultured in a culture medium that contains some carbohydrate, such as some sugar. The sugar can be any convenient sugar or a combination of sugars. Examples include dextrose, sucrose, glucose, fructose or a combination thereof. The amount of sugar can be included in amounts of about 1 g/liter to about 20 g/liter, or of about 3 g/liter to about 18 g/liter, or of about 5 g/liter to about 15 g/liter.

Fungi can be grown in PDB media (12 g/L potato dextrose broth, 5 g/L yeast extract, pH 5.3). In some cases the fungi and algae can initially be cultured together to form fungal/algae consortia in the presence of a simple medium that can contain small amounts of PDB media. For example, to form fungal/algae consortia a simple medium such as f/2 medium can be used that is supplemented with small amounts of PDB media.

| f/2 Medium | |
|---|---|
| NaNO$_3$ (75.0 g/L dH$_2$O) | 1.0 mL |
| Na$_2$SiO$_3$•9H$_2$O (30.0 g/L dH$_2$O) | 1.0 mL |
| f/2 Trace Metal Solution | 1.0 mL |
| f/2 Vitamin Solution | 0.5 mL |
| Filtered seawater to | 1.0 L |

Further information on the f/2 medium is available at a website describing the composition of f/2 media (algaeresearchsupply.com/pages/f-2-media).

In some cases, the fungal/algae consortia can be grown and maintained in a media that does not supply a nitrogen source (e.g., without nitrate or ammonium salts, or without other nitrogen-containing salts). For example, the fungus that is part of the fungal/algae consortia can supply a nitrogen source to the algae as well as providing for its own nitrogen needs.

Algae cells and fungal/algae consortia can, for example, be grown or maintained in minimal media such as f/2 media, or even in water (e.g., sea water) with little or no added nutrients, especially when the algae cells and fungal/algae consortia are exposed to light. For example, algae and fungal/algae consortia can be grown or maintained in continuous light (for example, at about 20 µmol photons/m$^2$/s to about 120 µmol photons/m$^2$/s, or at about 40 µmol photons/m$^2$/s to about 100 µmol photons/m$^2$/s, or at about 80 µmol photons/m$^2$/s).

Algae, fungi, and consortia of algae and fungi can be grown or maintained at a convenient moderate temperature. For example, algae, fungi, and consortia of algae and fungi can be grown or maintained at about 15° C. to 37° C., or about 18° C. to 32° C., or about 20° C. to 30° C., or at about room temperature.

Growing rather than non-growing cells and/or tissues can be used to generate consortia of algae and fungi. For example, log-phase cultures of algae can be used. Fungal tissues employed can include fungal mycelia and/or fungal mycelium. Fungal tissues can be chopped or cut up. For example, fungal tissues can be briefly blended or chopped into small pieces (0.1 to 4 cm, or 0.3 to 3 cm, or 0.5 to 2 cm) before combining the fungal tissues with algae.

Generating Fungal/Algal Consortia

To form consortia, the algal cells and fungal cells (or fungal tissues) can be mixed together in a selected culture media and incubated together for one or more days, one or more weeks, one or months, one or more years, or indefinitely. The culture media or growth conditions can be changed or modulated as desired to form and maintain the fungal/algal consortia.

To form the fungal/algal consortia, the fungal tissues/cells and the algal cells can be incubated in sufficient cell/tissue density so that the fungal tissues/cells and the algal cells come into contact. For example, algae can be added to fungal cells/tissues at a density of about $1 \times 10^4$ algae cells/mL to $1 \times 10^9$ algae cells/mL, or at a density of about $1 \times 10^5$ algae cells/mL to $1 \times 10^8$ algae cells/mL, or at a density of about $1 \times 10^6$ algae cells/mL to $1 \times 10^8$ algae, or at a density of about $1\text{-}3 \times 10^7$ cells/mL. The ratio of fungal tissues to algae cells can vary. In some cases, it may be useful to use more fungal tissue (by mass) than algal cell mass. For example, the ratio can vary from about 10:1 by mass fungal tissue to algal cells, to about 1:1 by mass fungal tissue to algal cells. In some cases, the ratio can vary from about 5:1 by mass fungal tissue to algal cells, to about 1:1 by mass fungal tissue to algal cells. For example, the ratio can be about 3:1 by mass fungal tissue to algal cells.

In some cases it may be useful to use more algae cell mass than fungal tissue mass. For example, the ratio can vary from about 10:1 by mass algal cells to fungal tissue mass, to about 1:1 by mass algal cells to fungal tissue mass. In some cases, the ratio can vary from about 5:1 by mass algal cells to fungal tissue mass to about 1:1 by mass algal cells to fungal tissue mass.

As indicated in the foregoing section, when initially preparing a consortium between one or more fungal species and one or more algae species, the fungi and algae can be cultured in a culture medium that contains some carbohydrate, such as some sugar. The sugar can be any convenient sugar or a combination of sugars. Examples include dextrose, sucrose, glucose, fructose or a combination thereof. The amount of sugar can be included in amounts of about 1 g/liter to about 20 g/liter, or of about 3 g/liter to about 18 g/liter, or of about 5 g/liter to about 15 g/liter.

The consortium between one or more fungal species and one or more algae species can be formed in a liquid media, in a semi-solid media, or on a solid media.

Consortia of algal cells within fungal tissues can include fungal hyphae with different numbers of algae cells within them. For example, fungal tissues can include 1 to 2000 algae cells per fungal hyphae, or 2 to 1700 algae cells per fungal hyphae, or 5 to 1500 algae cells per fungal hyphae, or 10 to 1000 algae cells per fungal hyphae, or 15 to 500 algae cells per fungal hyphae, or 5 to 100 algae cells per fungal hyphae. Fungal hyphae can typically have any number of algae cells within them, up to about 5000 algae cells.

Consortia Benefits

The fungal/algae consortia described herein can be more robust that separate cultures of algae or separate fungi. For example, the algae can provide it fungal partner with useful carbon-based nutrients while the fungus can provide its algae partner with useful nitrogen-based nutrients, or vice versa. Hence, the fungal/algae consortia described herein can be more tolerant of environmental stresses such as nutrient-poor conditions.

In addition, a fungal partner can protect its algae cells from environmental stresses such as salt imbalances (too much salt or too little) that would otherwise adversely affect the growth or health of the algae.

Algae are useful for production of useful compounds and materials such as oils, biofuels, nutrients (sugars, vitamins, proteins, etc.), and biomass. The protection and support provided by a fungal partner can help foster the growth and production of algae. Similarly, the algae can support and foster the growth of its fungal partner. Hence, the fungal/algae consortia described herein can be used to produce useful products under low cost conditions that do not require expensive monitoring and maintenance.

For example, fungal/algae consortia described herein can be used to produce various types of oils or biofuels. In certain aspects, the fungal-algae consortium can have lipid content greater than about 20%, and preferably greater than about 30% by weight of the consortium weight. Currently known algae species may contain a practical maximum lipid content of about 40% by weight, although levels as high as 60% have been reported. Such species can be algae partners for formation of fungal/algae consortia. In some embodiments, the lipid-producing consortium can comprise lipid content greater than 40%, 50%, 60%, 70%, 80%, or 90% by weight of the consortium. In a specific embodiment, the subject methods involve selection of consortium which produce high levels of simple and/or complex lipids.

For example, the content of lipids provided by cultures and methods described herein can be at least 20%, 30%, 40%, 50%, 60%, 70%, 80%, or 90% by weight of the consortium.

The following non-limiting Examples illustrate how aspects of the invention have been developed and can be made and used.

Example 1: Materials and Methods

This Example describes some of the materials and methods that were used in the development of the invention.

Strains and Growth Conditions

Marine alga *Nannochloropsis oceanica* CCMP1779 was obtained from Provasoli-Guillard National Center for Culture of Marine Phytoplankton and incubated as described by Vieler et al. (PLoS Genet. 8, e1003064 (2012)). In brief, *N. oceanica* cells were grown in flasks containing f/2 media under continuous light (~80 µmol/m$^2$/s) at 22° C. with agitation (100 rpm). Log-phase algal culture (1~3×10$^7$ cells/mL) was used for co-culture with fungi. Cell size and density of algal culture were determined using a Z2 Coulter Counter (Beckman). *Mortierella elongata* AG77 and NVP64 were isolated from soil samples collected at North Carolina, USA (AG77) and Michigan, USA (NVP64). *M. elongata* AG77 and NVP64 hosting bacterial endosymbiont had been cured of their endobacteria by a series of antibiotic treatments as described by Partida-Martinez et al. (Chembiochem. 8, 41-45 (2007)), and the resultant clean strains were used in this study. Other fungal isolates obtained from healthy surface sterilized *Populus* roots were obtained from the Plant-Microbial Interfaces (PMI) project (Bonito et al., Fungal Ecol. 22, 35-42 (2016)) (new strains). Fungi were incubated in flasks containing PDB media (12 g/L potato dextrose broth, 5 g/L yeast extract, pH 5.3) at room temperature (RT, ~22° C.).

For the co-culture of algae and fungi, fungal mycelia were briefly blended into small pieces (0.5 to 2 cm) using a sterilized blender (speed, 30 s). After 24-h recover in PDB medium, fungal tissues were collected by centrifugation (3,000 g for 3 min), washed twice with f/2 medium and resuspended in ~15 mL f/2 medium. A portion of fungal tissues (3-4 mL) were used for the calculation of dry biomass: 1 mL of fungal tissues were transferred with cut-off pipette tip and filtrated through pre-dried and pre-weighed Whatman GF/C filters and dried overnight at 80° C. Similar method was used for the measurement of alga biomass. Fungal tissues about 3 times of alga biomass were added into *N. oceanica* culture for co-cultivation on a shaker (~60 rpm) under continuous light (~80 µmol/m$^2$/s) at RT. After 18-days of co-culture, the shaker was turned off for free settling of algae and fungi overnight. Supernatant was removed with Pasteur pipettes and the same volume of fresh f/2 medium containing 10% PDB was added to the culture. After that, the alga-fungus co-culture was biweekly refreshed with f/2 medium supplemented with 10% PDB.

Nutrient deprivation of the co-culture was performed according to a published protocol for *N. oceanica* (Vieler et al., PLoS Genet. 8, e1003064 (2012)). Mid-log-phase *N. oceanica* cells (~1×10$^7$ cells/mL) grown in f/2 media (25 mL) were harvested by centrifugation and washed twice with nutrient-deficient f/2 media [without carbon (—C), nitrogen (—N) or phosphorus (—P)] and resuspended in 25 mL nutrient-deficient f/2 media, respectively. AG77 mycelia grown in PDB medium were washed twice with the nutrient-deficient f/2 and added into respective *N. oceanica* cultures for co-cultivation. To block carbon dioxide from air, the flasks of —C cultures were carefully sealed with Parafilm M® over aluminum foil wrap. Cell viabilities were analyzed by confocal microscopy after 10-d co-culture of —N and 20 d of —C and —P.

Light Microscopy

Interaction and symbiosis between algae and fungi were examined with an inverted microscope with differential interference contrast (DIC) and time-lapse modules (DMi8, Leica). DIC images were taken from the alga-fungus aggregates after short-term (6 days) and long-term (over one month) co-cultivation. To characterize the algal endosymbiosis in fungi, differential interference contrast (DIC) and time-lapse photography were performed using different period of long-term co-culture of algae and fungi (from 1 to 6 months). Alga-fungus aggregates grown in flasks were transferred to 35 mm-microwell dish (glass top and bottom, MatTek) and embedded in a thin layer of soft-solid f/2 medium supplemented with 10% PDB and 0.25% low gelling temperature agarose (Sigma-Aldrich) that immobilized cells for microscopy. Morphology of different age green hyphae (AG77 hyphae containing intracellular $N.$ $oceanica$ cells) was recorded in DIC micrographs (FIG. 4A to 4E), as well as real-time videos that showed four groups of green hyphae with manually adjusted focus. Videos were put side by side in a movie (data not shown) using video-editing software VideoStudio X9 (Corel). To investigate the establishment of algal endosymbiosis in fungi, randomly selected alga-fungus aggregates from 35-d co-culture were incubated and observed in 35 mm-microwell dish containing soft-solid f/2 medium with 10% PDB and 0.25% agarose up to two weeks. Time-lapse photographs were combined together to create another movie (data not shown) with VideoStudio.

Scanning Electron Microscopy

SEM was performed to investigate the physical interaction between $N.$ $oceanica$ and $M.$ $elongata$ at the Center for Advanced Microscopy of Michigan State University (CAM, MSU). Alga-fungus aggregates from 6-d co-culture of $N.$ $oceanica$ and $M.$ $elongata$ (AG77 or NVP64) were fixed in 4% (v/v) glutaraldehyde solution and dried in critical point dryer (Model 010, Balzers Union). After drying, the samples were mounted on aluminum stub using high vacuum carbon tabs (SPI Supplies) and coated with osmium using a NEOC-AT osmium coater (Meiwafosis). Processed exocarp tissues were examined using a JSM-7500F scanning electron microscope (Japan Electron Optics Laboratories).

Confocal Microscopy

Figure 3A:
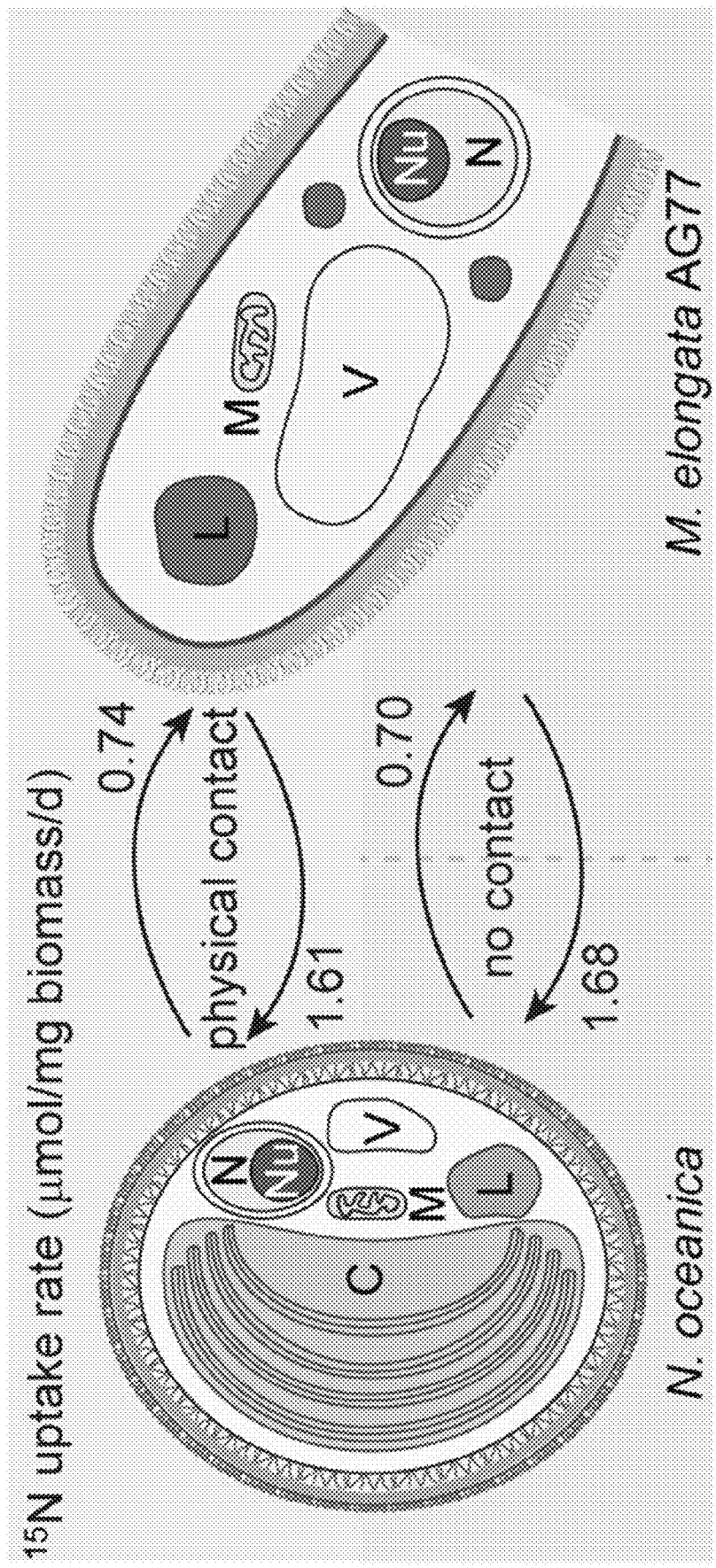
FIGS. 3A-3J illustrate that *N. oceanica* benefits from co-culture with *M. elongata*.
Figure 3B:
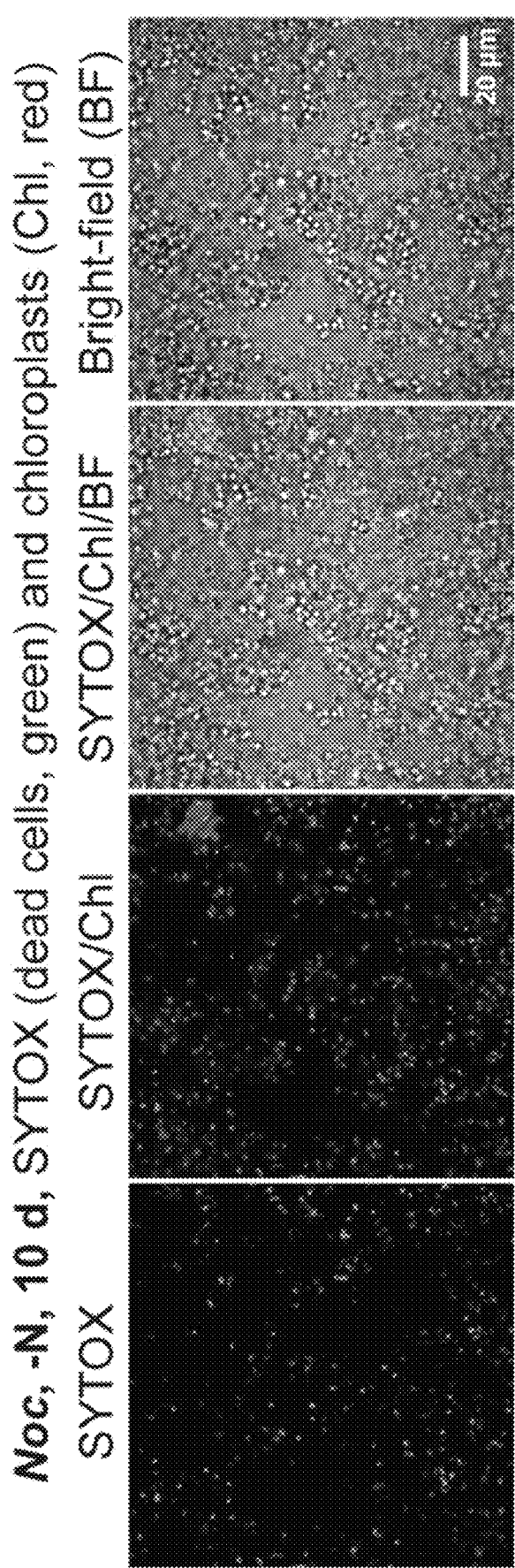
Figure 3C:
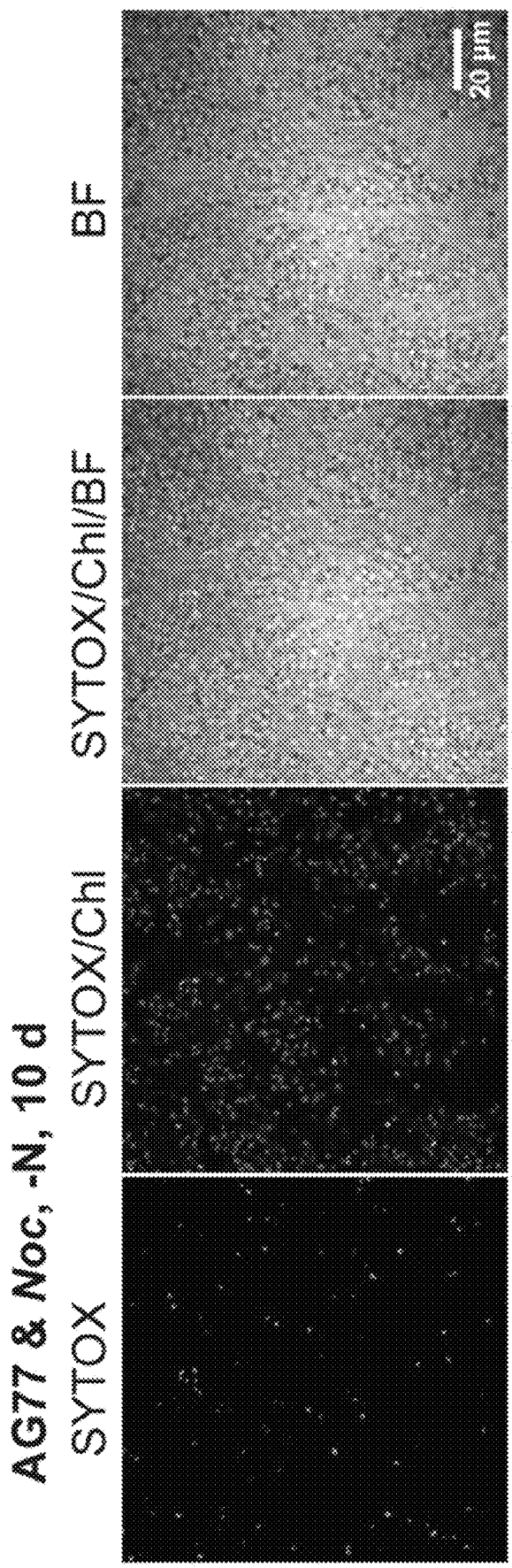
Figure 3E:
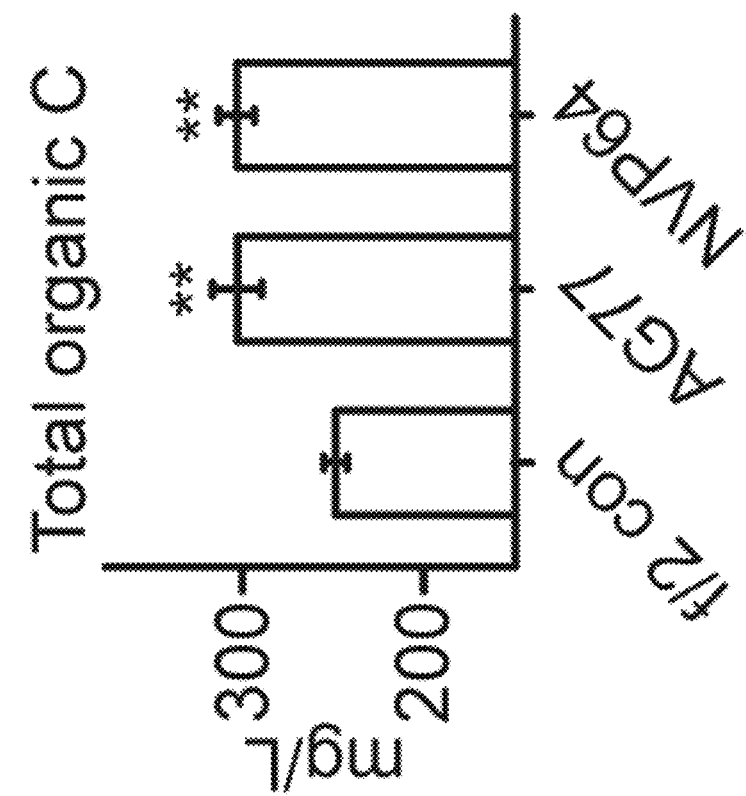
Figure 3D:
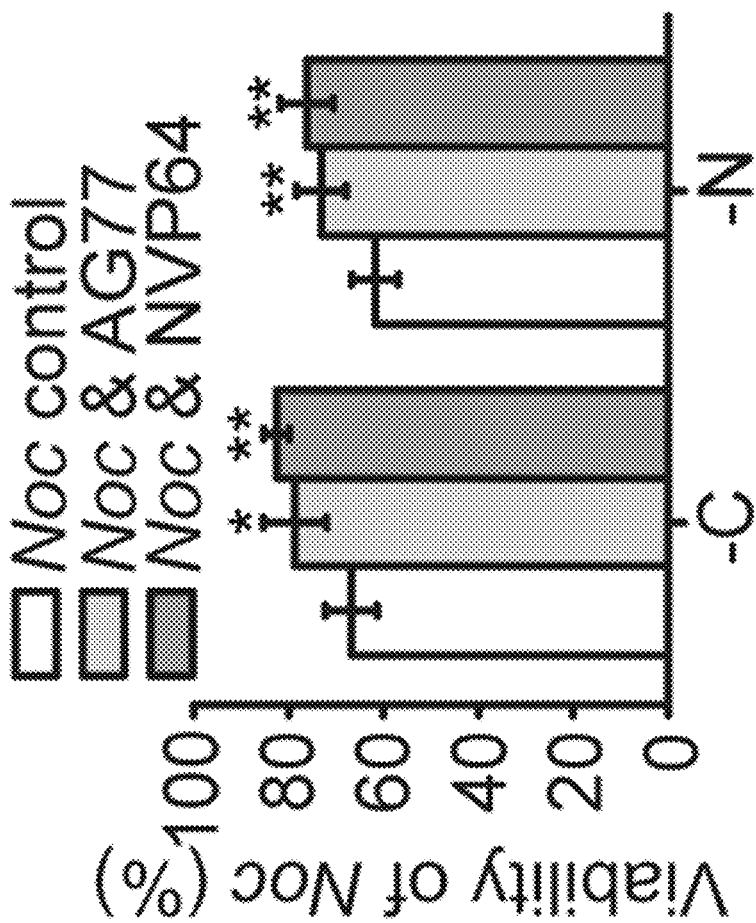
Figure 3F:
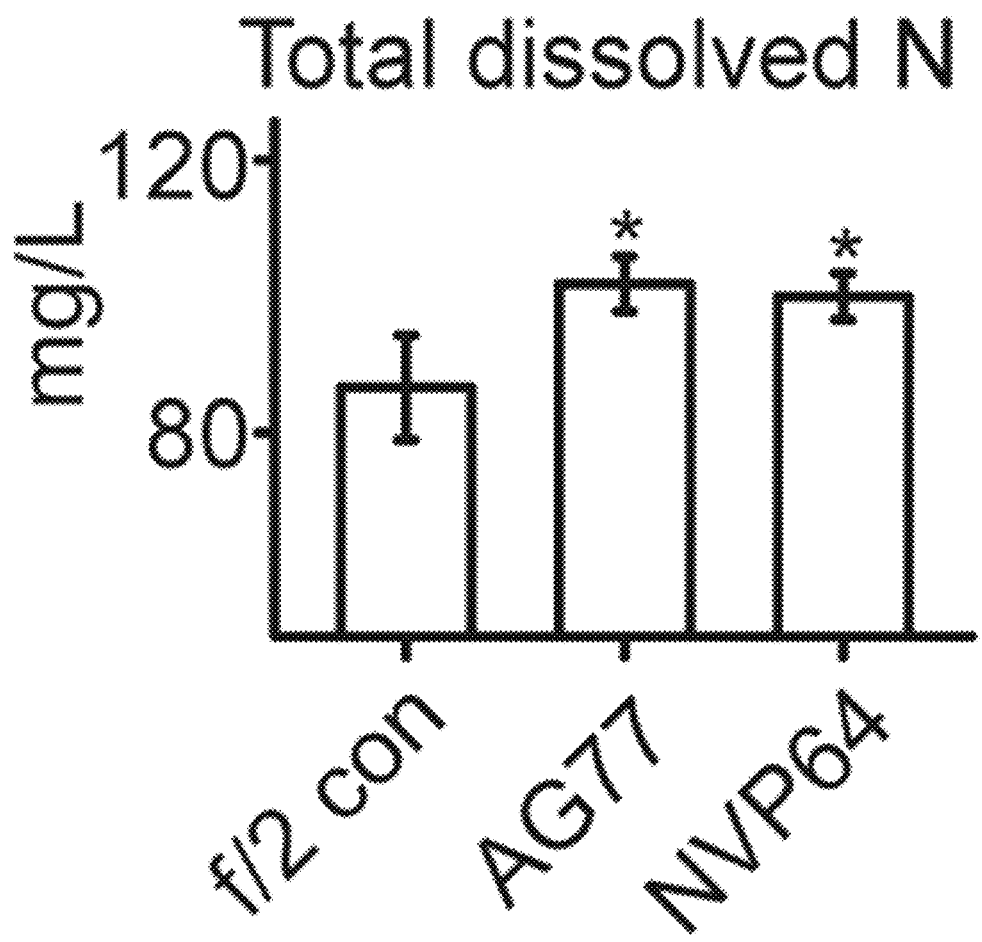

Viability of $N.$ $oceanica$ and $M.$ $elongata$ cells (e.g., during their co-culture) was determined by confocal microscopy using a confocal laser scanning microscope FluoView 1000 (Olympus) at CAM, MSU. SYTOX® Green nucleic acid stain (Molecular Probes, Life Technologies), a green-fluorescent nuclear and chromosome counterstain impermeant to live cells, was used to indicate dead cells of algae and fungi following a protocol described by Tsai et al. (Proc. Natl. Acad. Sci. U.S.A. 111, 15833-15838 (2014)). Briefly, 1 µL of 5 mM SYTOX Green was added to 1 mL of cell culture and incubated for 5 min in the dark at room temperature. Samples were washed twice with f/2 medium before observation (SYTOX Green, 488 nm excitation, 510 to 530 nm emission; chlorophyll, 559 nm excitation, 655 to 755 nm emission). Viability of $N.$ $oceanica$ cells was analyzed using ImageJ software. Cell viability was analyzed during alga-fungus co-culture in flasks containing f/2 medium (1, 4 and 7 days) to investigate whether the cells were living or dead during the 7-day co-culture of $^{14}$C- and $^{15}$N-chasing experiments. Viability of $N.$ $oceanica$ cells co-cultivated with $M.$ $elongata$ AG77 and NVP64 under nutrient deprivations (without a nitrogen source (—N), without a carbon source (—C), and/or without a phosphate source (—P)) was tested to evaluate whether $N.$ $oceanica$ benefits from the co-culture with $Mortierella$ fungi (FIG. 3B-3D). Viability of $M.$ $elongata$ AG77 was analyzed during its 30-day incubation in f/2 medium to check whether the cells were living or dead when the culture media were collected for nutrient analyses (total organic C and dissolved N, FIG. 3F-3G).

Localization of $N.$ $oceanica$ cells in alga-fungus aggregates was investigated by cell-wall staining using Wheat Germ Agglutinin Conjugate Alexa Fluor® 488 (WGA, Molecular Probes) following the manufacturer's instruction. In brief, alga-fungus aggregates were collected by centrifugation and washed once with PBS buffer (pH7.2), followed by addition of 5 µg/mL WGA and incubation at 37° C. for 10 min. Samples were washed twice with f/2 medium and observed under the FluoView 1000 microscope (WGA, 488 nm excitation, 510 to 530 nm emission; chlorophyll, 559 nm excitation, 655 to 755 nm emission).

Transmission Electron Microscopy

Figures 4A, 4B, 4C:
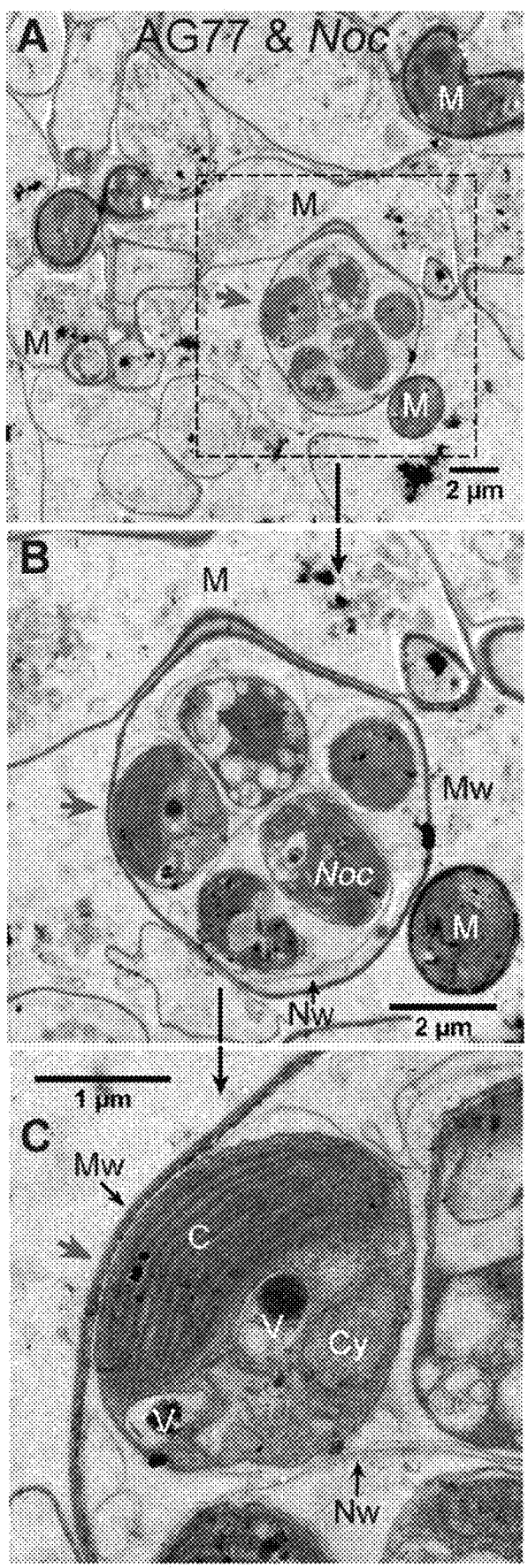
Figures 4D, 4E, 4F:
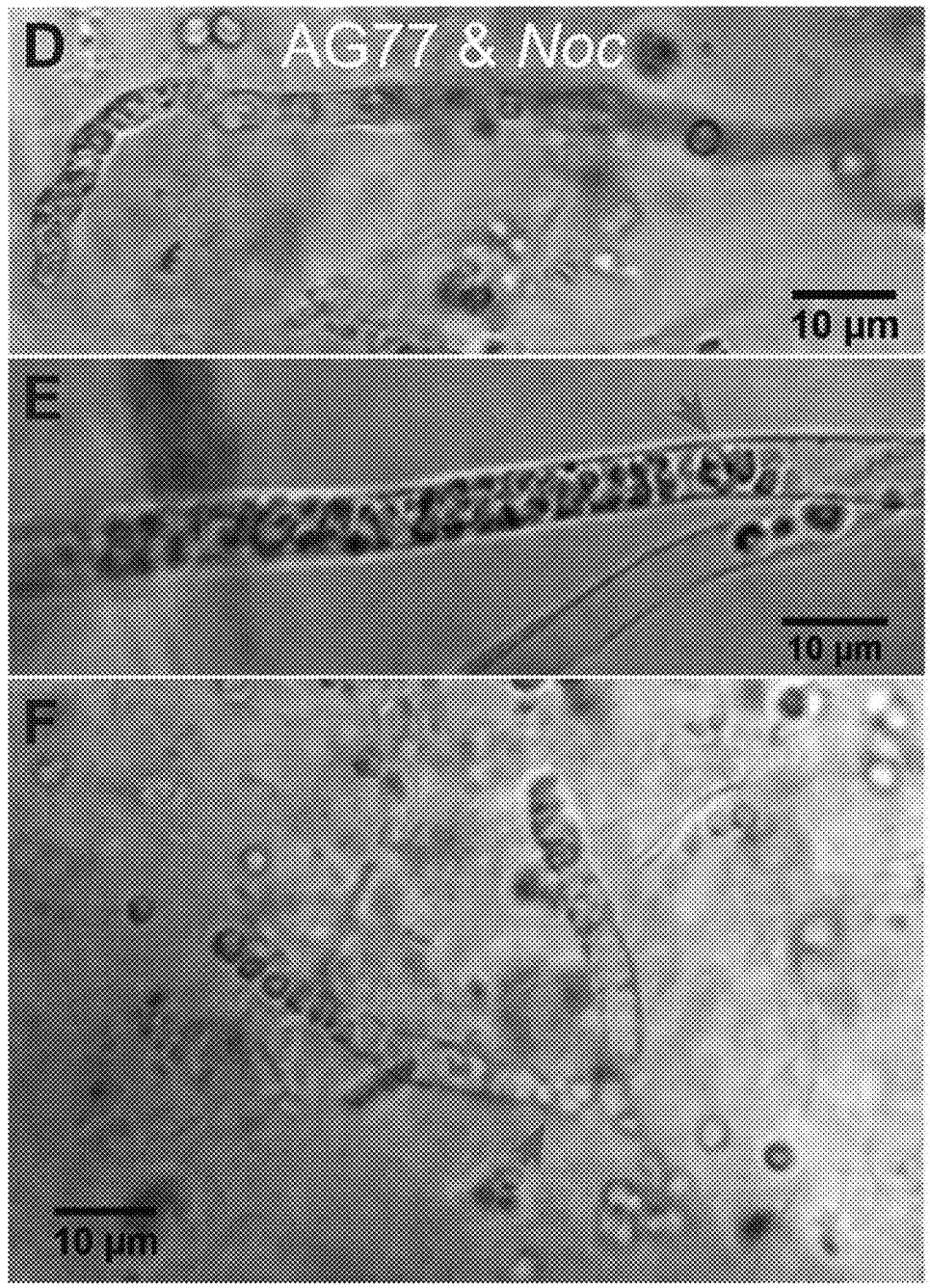
Figure 4G:
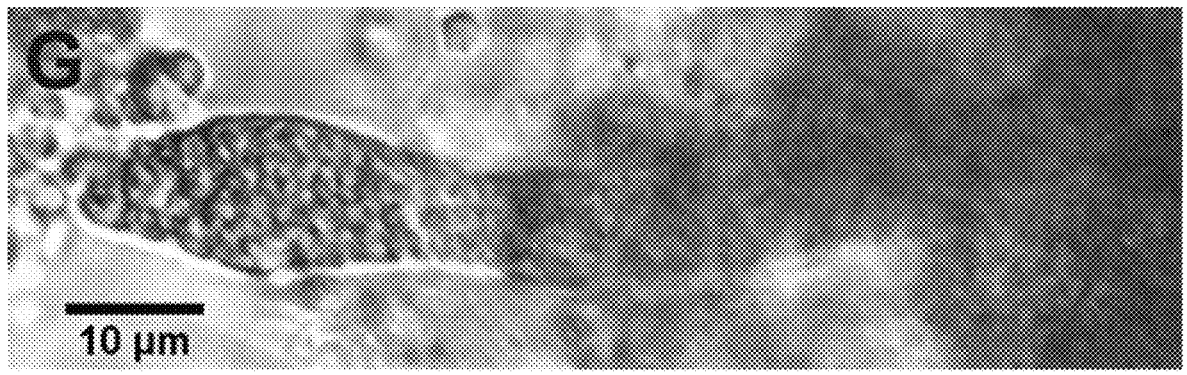
Figure 4H:
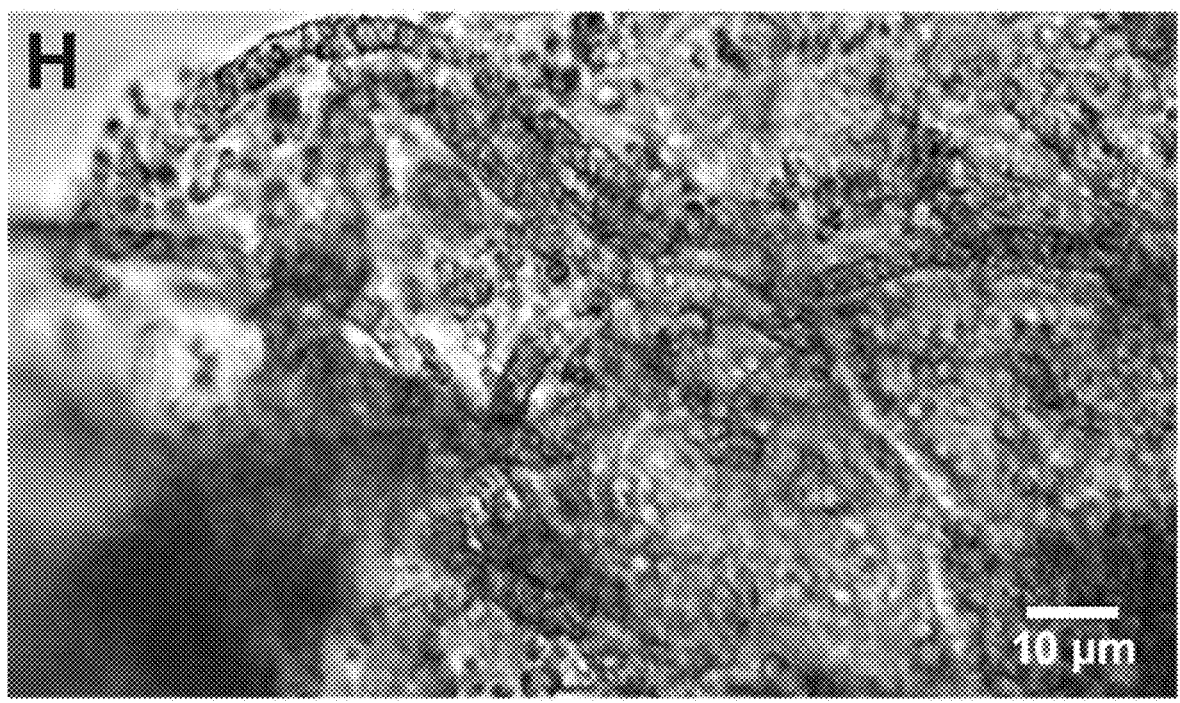
Figures 5E, 5F:
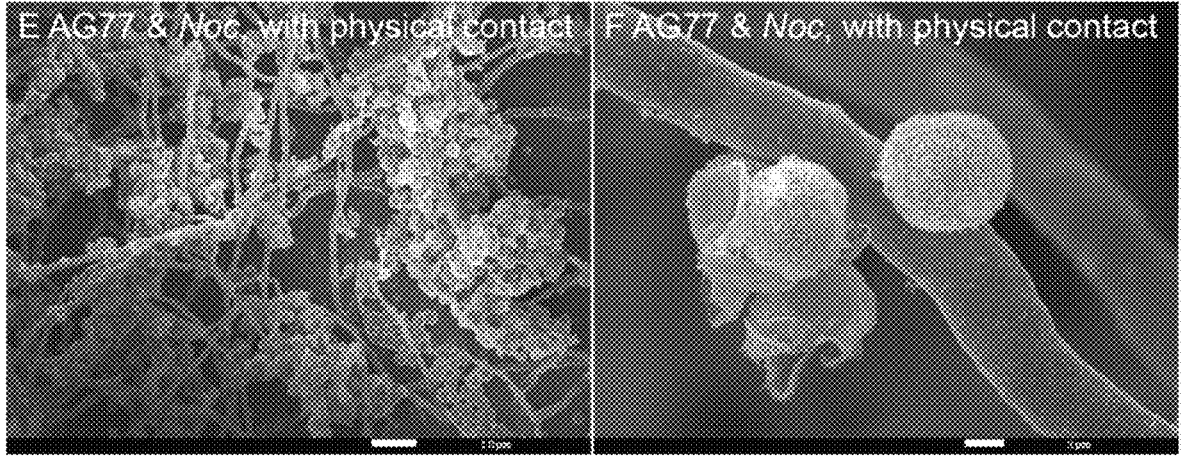
Figures 5G, 5H:
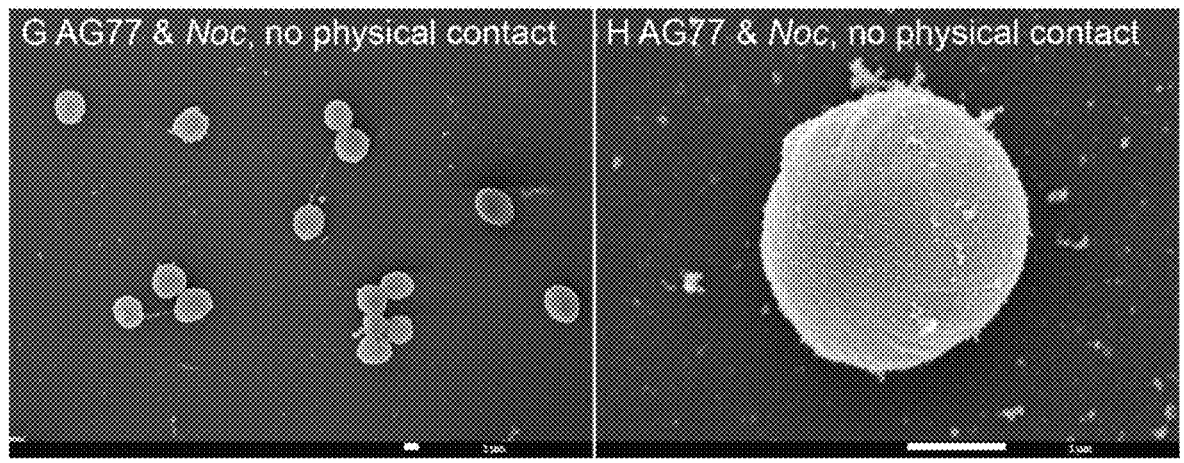

TEM was performed on $Nannochloropsis$ $oceanica$ and $Mortierella$ aggregates co-cultured for about one month. Randomly collected alga-fungus aggregates were fixed overnight at 4° C. in sodium cacodylate buffer (50 mM, pH 7.2) supplemented with 2.5% (v/v) glutaraldehyde. The fixed samples were washed three times with sodium cacodylate buffer, post-fixed in 1% $OsO_4$ (v/v) for 2 hours at room temperature and then washed three times with sodium cacodylate buffer. After dehydration through a graded series of ethanol and acetone, samples were infiltrated with a series of acetone/resin Epon/Araldite mixtures and finally embedded in resin Epon/Araldite mixture (Electron Microscopy Sciences). Ultrathin sections (70 nm) were cut with an ultramicrotome (RMC Boeckeler) and mounted onto 150 mesh formvar-coated copper grids, followed by staining with uranyl acetate for 30 min at room temperature. The sections were then washed with ultrapure water and stained 10 min with lead citrate and used for observation. Images were taken with a JEOL100 CXII instrument (Japan Electron Optics Laboratories) equipped with SC1000 camera (Model 832, Gatan) and processed with ImageJ (FIG. 4F-4H).

Example 2: Methods for Evaluating Nutrient Exchange Between Fungi and Algae

Light microscopy and SEM showed tight physical interaction between soil fungus $Mortierella$ $elongata$ and the marine algae $Nannochloropsis$ $oceanica$. This Example describes experiment procedures for evaluating whether metabolic exchanges occur between $N.$ $oceanica$ and $M.$ $elongata$.

Isotope labeling and chasing experiments were performed using labeled carbon and nitrogen ($^{14}$C and $^{15}$N) nutrients for $N.$ $oceanica$ and $M.$ $elongata$. For $^{14}$C assays, 20 µL of [$^{14}$C]sodium bicarbonate (1 mCi/mL, 56 mCi/mmol, American Radiolabeled Chemicals) was added to 20 mL of early log-phase culture of $N.$ $oceanica$ (~2×10$^6$ cells/mL) and incubated for 5 days when the $^{14}$C incorporation reached ~40%. The $^{14}$C-labeled $N.$ $oceanica$ cells were harvested by centrifugation (4,000 g for 10 min) and washed three times with f/2 medium. The supernatant of the last wash was analyzed in Bio-Safe II counting cocktail (Research Products International) using a scintillation counter (PerkinElmer 1450 Microbeta Trilux LSC), to confirm that $^{14}$C-labeling medium was washed off. The pellet of $^{14}$C-labeled *N. oceanica* was resuspended in 20 mL f/2 medium. Subsequently, non-labeled *M. elongata* AG77 mycelia (~3 times of algae biomass, intact cells without blending) grown in PDB medium were washed twice with f/2 medium and added to the 20 mL $^{14}$C-labeled algal culture for 7-d co-cultivation. Alga-fungus aggregates were then harvested by PW200-48 mesh (Accu-Mesh) and algal cells in the flow through were collected by centrifugation (4,000 g for 10 min) and kept as the first part of $^{14}$C-labeled alga control. Alga-fungus aggregates were intensively washed in 50 mL conical centrifuge tube containing 40 mL of f/2 medium using a bench vortex mixer (~1500 rpm, 15 min). Fungal mycelia were collected by NITEX 03-25/14 mesh (mesh opening 25 µm, SEFAR), and algal cells in the flow through were harvested by centrifugation and stored as the second fraction of $^{14}$C-labeled alga control. Mesh-harvested fungal mycelia (with obviously reduced amount of algae attached) were added to 1.5 mL microcentrifuge tube containing 300 µL of PBS buffer (pH 5.0) supplemented with 4% hemicellulase (Sigma-Aldrich) and 2% driselase (Sigma-Aldrich) and incubated overnight at 37° C. This step was performed to digest the algal cell walls (Chen et al. J. Phycol. 44, 768-776 (2008)). After cell-wall digestion, 700 µL of f/2 medium was added and algae were separated from fungi by intensive vortex for 15 min. Fungal mycelia were collected by NITEX 03-25/14 mesh while the flow-through was kept as the last fraction of alga control. Three fractions of $^{14}$C-labeled alga controls were combined together while fungi were washed three times with f/2 medium. Half of the samples were dried and weighed for biomass and the others were used for $^{14}$C measurements. To examine cross contamination after alga-fungus isolation, non-radioactive samples were processed the same way and analyzed by light microscopy and PCR. PCR primers were used that were specific for the *N. oceanica* gene encoding Aureochrome4 (AUREO4), a blue light-responsive transcription factor that only conserved in photosynthetic stramenopiles such as *N. oceanica*: Aureo4pro F+ (5'-AGAGGAGCCATGGTAG-GAC-3'; SEQ ID NO:1) and Aureo4 DNAD R− (5'-TCGT-TCCACGCGCTGGG-3'; SEQ ID NO:2). Primers specific for *M. elongata* were also used, including genes encoding translation elongation factor EF1a and RNA polymerase RPB1: EF1αF (5'-CTTGCCACCCTTGCCATCG-3'; SEQ ID NO:3) & EF1αR (5'-AACGTCGTCGTTATCGGACAC-3'; SEQ ID NO:4), RPB1F (5'-TCACGWCCTCCCATG-GCGT-3'; SEQ ID NO:5) and RPB1R (5'-AAGGAGGGTCGTCTTCGTGG-3'; SEQ ID NO:6).

Isolated algae and fungi were frozen by liquid nitrogen and ground into fine powders by steel beads and TissueLyser II (QIAGEN), followed by lipid extraction in 1.2 mL chloroform:methanol (2:1, v/v) with vortex for 20 min. Double-distilled water (ddH$_2$O, 100 µL) was added to the samples, briefly mixed by vortex and then centrifuged at 15,000 g for 10 min. Organic phase was collected as total lipids. One mL of 80% methanol (v/v) was added to the water phase and cell lysis to extract free amino acids (FAAs). After centrifugation at 20,000 g for 5 min, supernatant was kept as total FAAs and the pellet was air-dried and used to extract protein with 200 µL of SDS protein extraction buffer at 42° C. for 15 min. After centrifugation at 10,000 g for 10 min, supernatant (~200 µL) was collected for further protein precipitation (−20° C., 1 h) with the addition of 800 µL pre-cold acetone, while the pellet was kept for carbohydrate analyses. Total proteins (pellet) and soluble compounds (supernatant) were separated by centrifugation at 20,000 g for 15 min after protein precipitation. The pellet of total proteins was resuspended in 200 µL of SDS protein extraction buffer for scintillation counting. The pellet of carbohydrates was air-dried, resuspended in 200 µL ethanol, transferred to glass tube with Teflon-liner screw cap, and then dissolved by 2 to 4 mL of 60% sulfuric acid (v/v) according to described protocols (Velichkov, World J. Microbiol. Biotechnol. 8: 527-528 (1992); Scholz et al., Eukaryot. Cell. 13, 1450-1464 (2014)). Vortex and incubation at 50° C. were performed for the hard ones. Total lipids and soluble compounds were counted in 3 mL of xylene-based 4a20 counting cocktail (Research Products International), whereas total FAAs, proteins and carbohydrates were counted in 3 mL of Bio-Safe II counting cocktail. $^{14}$C radioactivity of the samples (dpm, radioactive disintegrations per minute) was normalized to their dry weight (dpm/mg).

To examine carbon transfer from fungi to algae, 200 µL of 0.1 mCi/mL [$^{14}$C]D-glucose (268 mCi/mmol, Moravek Biochemicals) or 100 µL of 1 mCi/mL [$^{14}$C]sodium acetate (55 mCi/mmol, American Radiolabeled Chemicals) were added to 20 mL of *M. elongata* AG77 grown in modified Melin-Norkrans medium [MMN, 2.5 g/L D-glucose, 0.25 g/L (NH4)$_2$HPO4, 0.5 g/L KH$_2$PO4, 0.15 g/L MgSO4, 0.05 g/L CaCl$_2$]. After 5-d $^{14}$C-labeling, fungal mycelia were harvested and washed three times with f/2 medium. Supernatant of the last wash was confirmed clean of $^{14}$C with scintillation counting. $^{14}$C-labeled fungi were added to 20 mL of *N. oceanica* culture for a 7-day co-culture. Alga-fungus aggregates were harvested using PW200-48 (first filtration) and NITEX 03-25/14 (second filtration) meshes. Algae in the flow-through were harvested and washed twice with f/2 medium by centrifugation and kept as free *N. oceanica* (unbound algal cells). The rest steps of sample preparation and $^{14}$C measurement was performed in the same way as described above.

To test whether physical contact is necessary for the carbon exchange between *N. oceanica* and *M. elongata*, $^{14}$C-labeling and chasing experiments were carried out using standard 6-well cell culture plates coupled with cell culture inserts that have a bottom made by hydrophilic polytetrafluoroethylene membrane filters (pore size of 0.4 µm, Millipore) to grow algae and fungi together with metabolic exchange but without physical contact. $^{14}$C-labeling was performed in the same way as described above. For alga-fungus co-culture, $^{14}$C-labeled algae (or fungi) were added in either plate wells or cell culture inserts while respective fungi (or algae) were grown separately in the inserts or plate wells to examine cross contamination. After 7-day co-culture, algae and fungi grown in the insert-plate system were easily separated by moving the insert to adjacent clean well. Samples were then processed following the protocol described above (without the steps of mesh filtration and cell-wall digestion).

Considering that *Mortierella* fungi are saprotrophic. Experiments were performed that involved $^{14}$C-labeling and chasing experiments using heat-killed $^{14}$C-cells to test whether algae and fungi utilize $^{14}$C from dead cells. Briefly, $^{14}$C-labeled algae or fungi were washed three times with f/2 medium and incubated in a water bath at 65° C. for 15 min, which killed the cells without causing serious cell lyses and addition of chemicals. Heat-killed $^{14}$C-algae (or fungi) were co-cultivated with unlabeled fungi (or algae) for 7 days in flasks. Subsequently, algae and fungi were separated by cell-wall digestion and mesh filtration, and $^{14}$C radioactivity of the samples was measured by scintillation counting as described above.

Nitrogen is another major nutrient for *N. oceanica* and *Mortierella*. Nitrogen exchange between *N. oceanica* and *M. elongata* was tested by $^{15}$N-labeling and chasing experiments using isotope ratio mass spectrometry. For $^{15}$N labeling of algae and fungi, *N. oceanica* cells were inoculated and grown in 200 mL of $^{15}$N-f/2 medium containing ~5% of [$^{15}$N]potassium nitrate [$^{15}$N/($^{15}$N+$^{14}$N), mol/mol], while *M. elongata* mycelia were inoculated and incubated in 2 L of $^{15}$N-MMN medium containing ~5% of [$^{15}$N]ammonium chloride for two weeks. Algal culture was diluted by the addition of fresh $^{15}$N-f/2 medium to maintain cell density at log phase. $^{15}$N-labeled *N. oceanica* cells from a 4 liter culture and $^{15}$N-labeled *M. elongata* mycelia from a 2 liter culture were harvested and a portion of the samples was kept as $^{15}$N-labeled controls. The rest of the sample was added to unlabeled cells in flasks (with physical contact) or to unlabeled cells in 6-well-culture plates with inserts (no physical contact) for a 7-day co-cultivation. Algae and fungi were separated after the co-culture as described above. Samples were then washed three times with ddH$_2$O. Fungal mycelia were homogenized in TissueLyser II (QIAGEN) using steel beads. Algae and fungi were then acidified with 1.5 to 3 mL of 1 N HCl, dried in beakers at 37° C. and weighed for biomass. Isotopic composition of algae or fungi ($\delta^{15}$N, ratio of stable isotopes $^{15}$N/$^{14}$N) and nitrogen (N) content (% N) were determined using a Eurovector (EuroEA3000) elemental analyzer interfaced to an Elementar Isoprime mass spectrometer following standard protocols (Fry et al., Rapid Commun. Mass Spectrom. (2007)). The N uptake rates (μmol N/mg biomass/day) of $^{15}$N-labeled *N. oceanica* cells from the media (medium-N, isotope dilution) and that of AG77 from $^{15}$N-labeled *N. oceanica*-derived N ($^{15}$N) were calculated based on the Atom % $^{15}$N [$^{15}$N/($^{15}$N+$^{14}$N)100%], % N and biomass following a protocol by Ostrom et al. (2016). The N uptake rates of $^{15}$N-AG77 from the media and that of recipient *N. oceanica* from $^{15}$N-AG77-derived N ($^{15}$N) were calculated in the same way.

Carbon and Nitrogen Measurements

Total organic carbon (TOC) and total dissolved nitrogen (TDN) in the media of *Mortierella* cultures were measured with a TOC-Vcph carbon analyzer with total nitrogen module (TNM-1) and ASI-V autosampler (Shimadzu) (FIG. 3F-3G). *M. elongata* AG77 and NVP64 were incubated for 18 days in flasks containing 25 mL of f/2 medium. Fungal tissues were removed by filtration with 0.22 micron filters (Millipore) and the flow-through was subject to TOC and TDN analyses.

Example 3: Carbon Nutrient Exchange Between Fungi and Algae

To test whether carbon or nitrogen exchange underlies the interaction between the soil fungus *Mortierella elongata* AG77 and the marine algae *Nannochloropsis oceanica*, a series of experiments were conducted using reciprocally $^{14}$C- and $^{15}$N-labeled algal and fungal partners. For carbon exchange assays algal cells were labeled with [$^{14}$C]-sodium bicarbonate and co-cultivated with non-labeled hyphae in flasks for one week. Conversely, fungal hyphae were grown in either [$^{14}$C]-glucose- or [$^{14}$C]-acetate-containing medium, then were co-incubated with non-labeled algal cells in flasks that allowed the two organisms to interact physically. Co-cultured algal and fungal cells were separated from each other by mesh filtration and were then analyzed for $^{14}$C exchange.

Figures 1, 2, 2A:
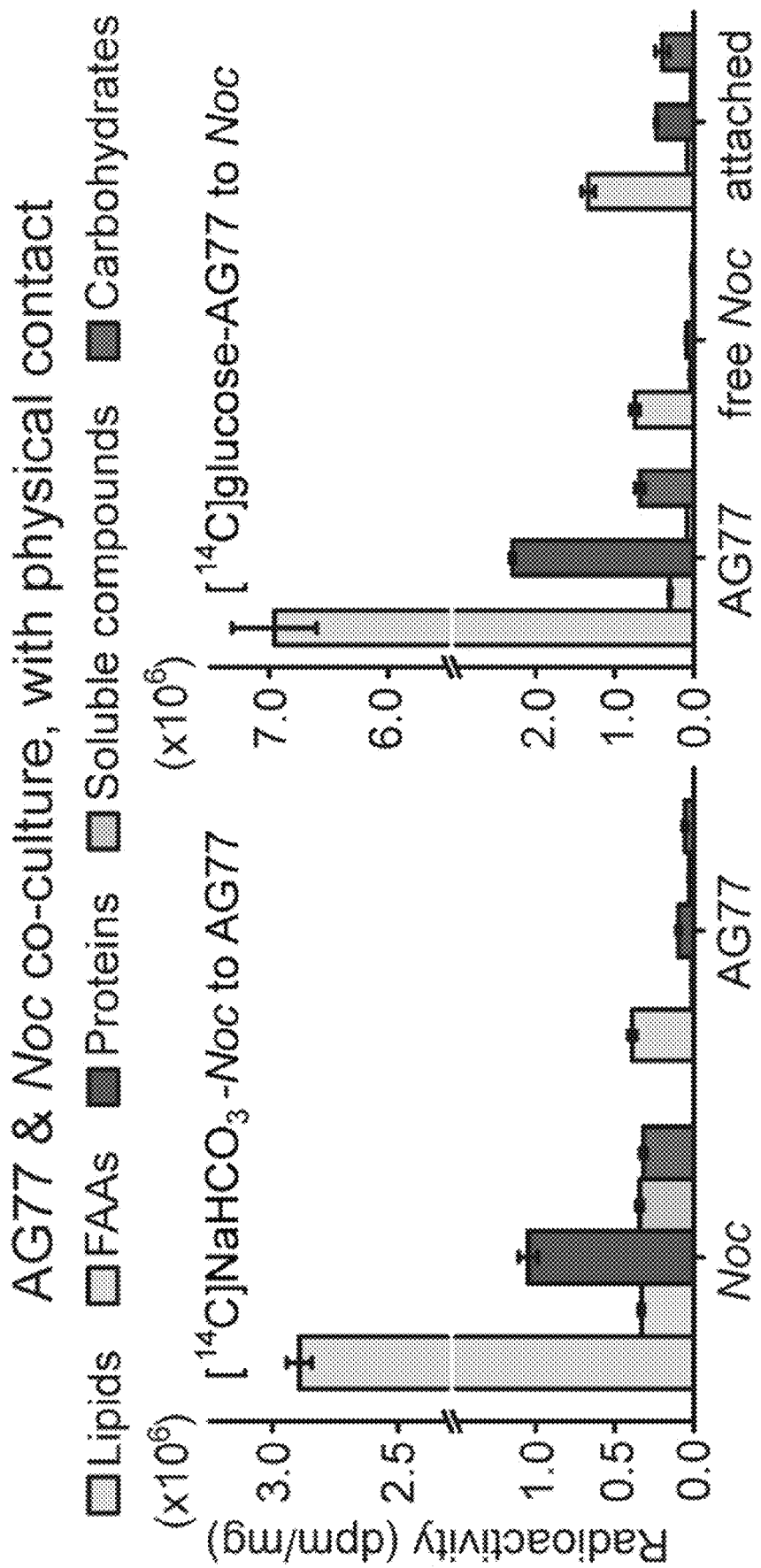

FIG. 2A-1 shows that $^{14}$C-carbon is transferred from the alga (*Nannochloropsis oceanica*; Noc) to the fungus (*Mortierella elongata* AG77). Nearly 70% of the transferred $^{14}$C-carbon was incorporated into the fungal lipid pool. Similarly, $^{14}$C-carbon transfer was observed from the labeled fungus (*Mortierella elongata* AG77) to its algal recipient (*Nannochloropsis oceanica*; Noc) (FIG. 2A-2). Intriguingly, algal cells attached to the fungal hyphae acquired more $^{14}$C than unattached cells grown in the same flask (FIG. 2A).

Figures 1, 2, 2B:
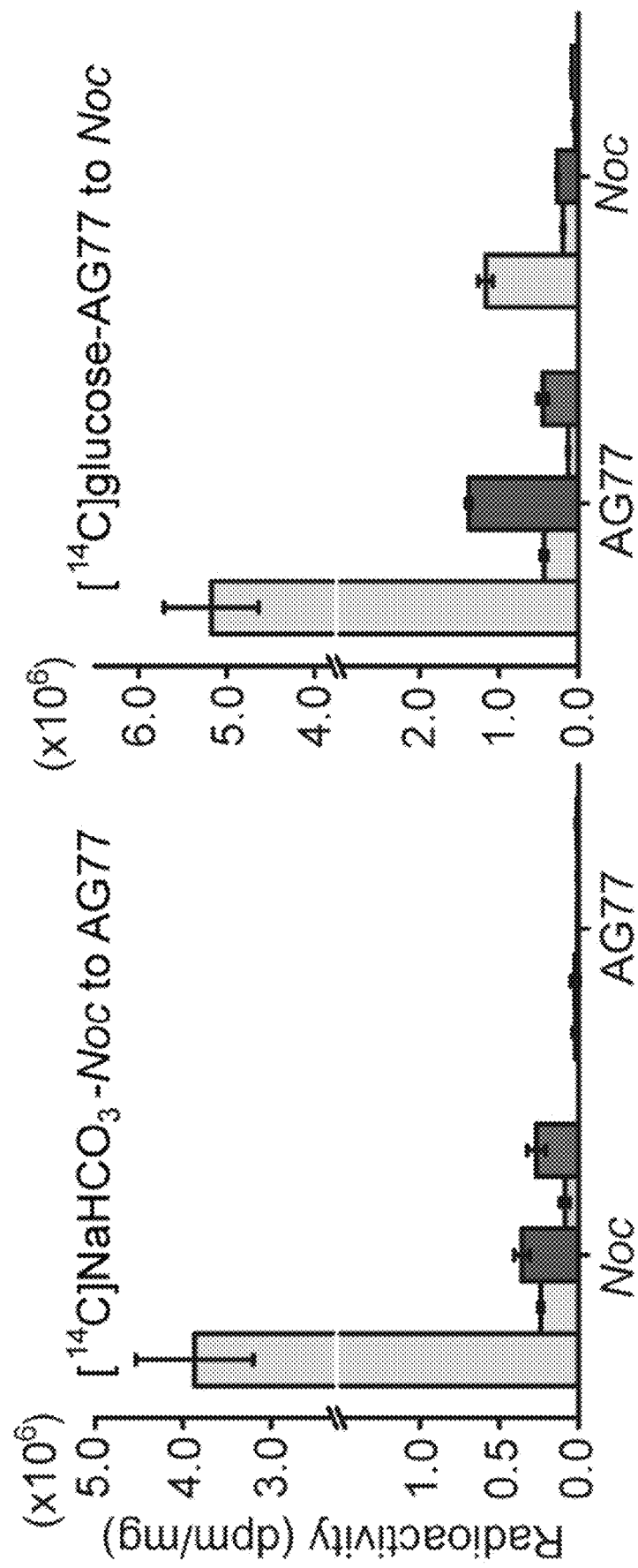
Figure 2C:
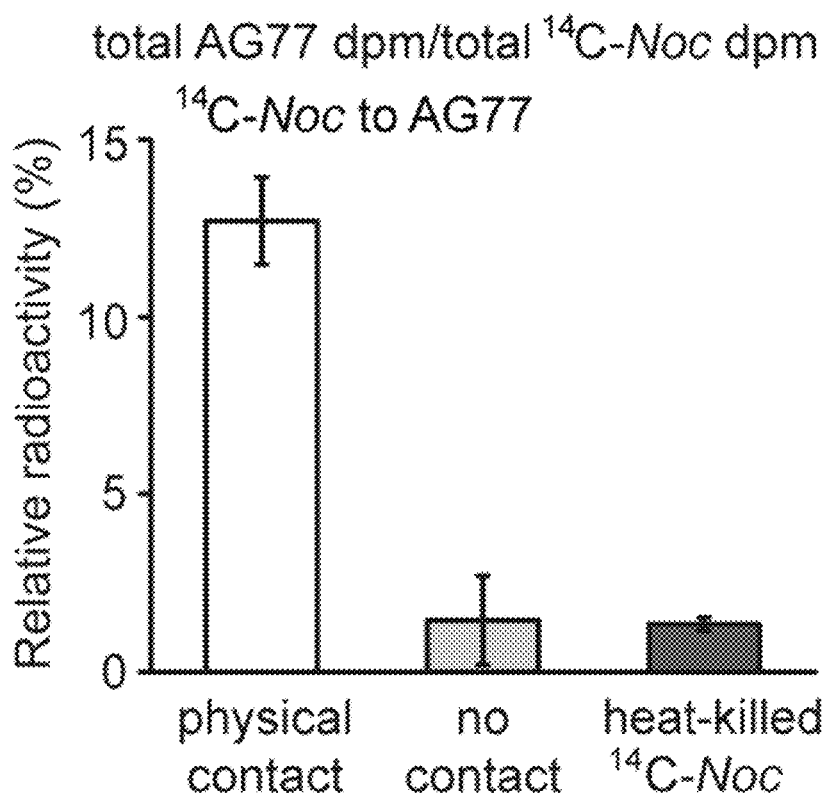
Figure 2D:
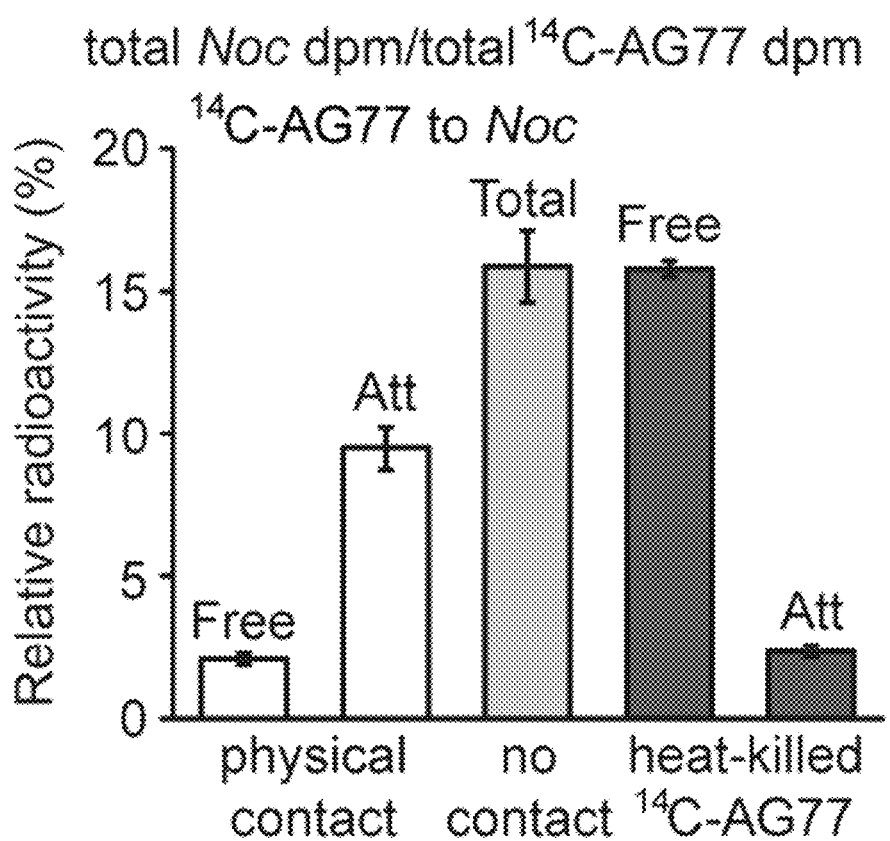
Figure 2E:
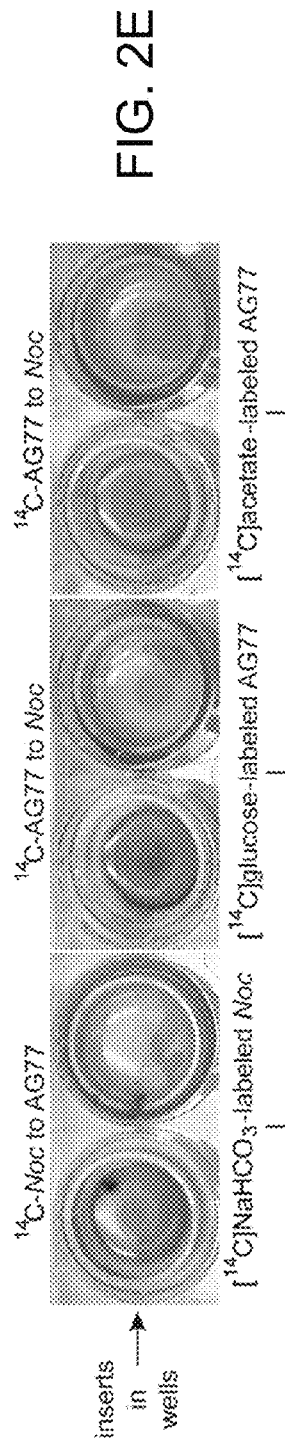
Figure 2F:
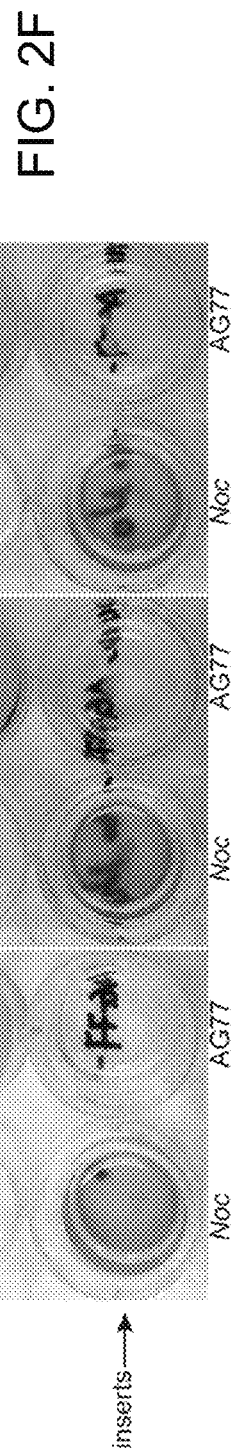
Figure 2G:
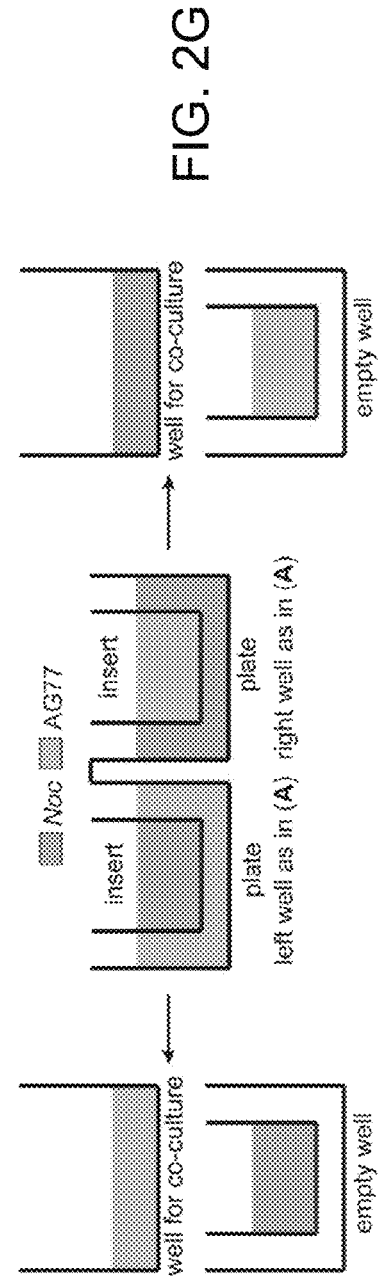
Figure 2H:
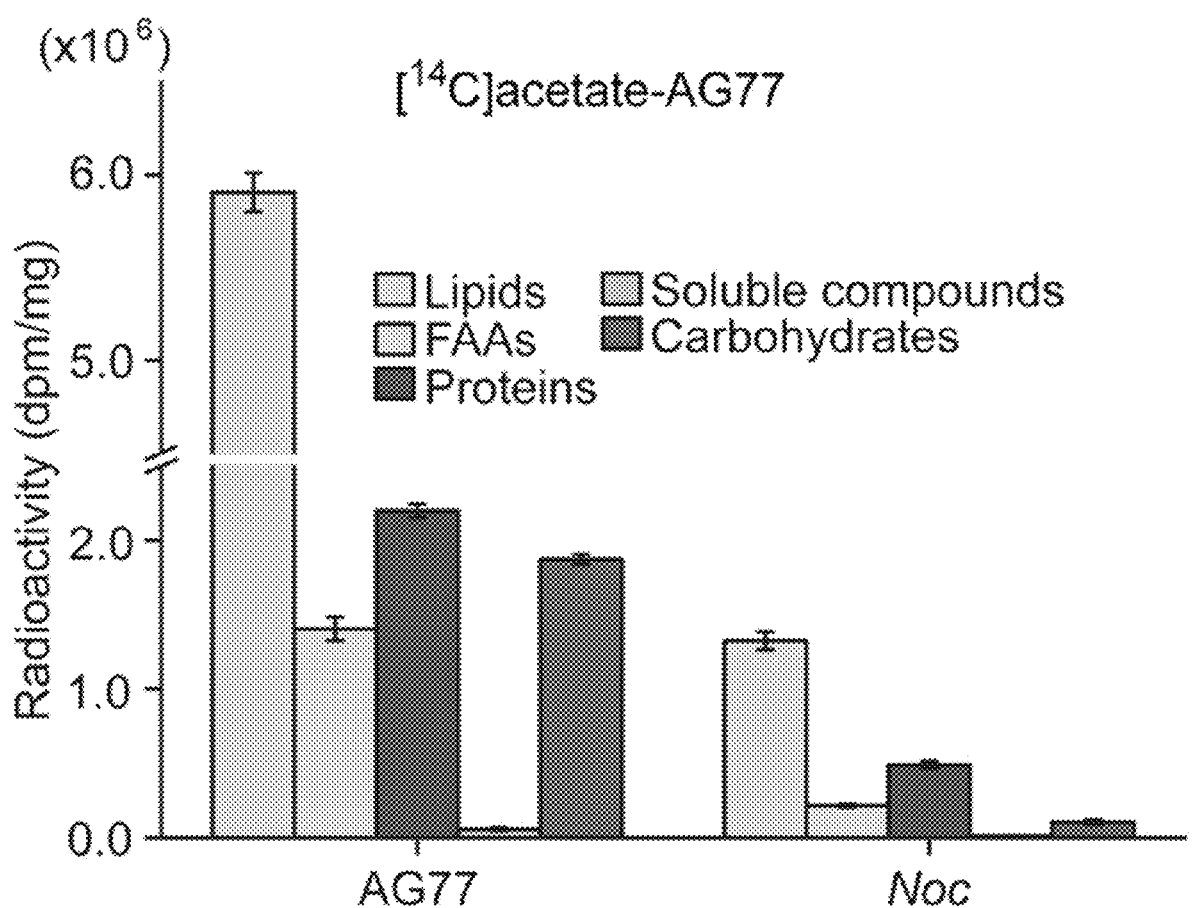

To further assess whether a physical interaction is required for carbon exchange between the photosynthetic alga and the putative fungal saprotroph, membrane inserts were used to physically separate reciprocally $^{14}$C-labeled algal and fungal partners (FIG. 2E-2H). These experiments showed that the physical contact between the algae and fungus is essential for $^{14}$C-carbon transfer to the fungus (FIG. 2B-2C), but is not necessary for $^{14}$C-carbon transfer to the algal cells (FIG. 2B, 2D and FIG. 2H).

*Mortierella* is regarded as a saprotroph that acquires carbon from dead organic matter. Experiments were performed, first, to test whether alga-derived carbon obtained by *Mortierella elongata* was due to the consumption of algal detritus. The $^{14}$C-labeling experiment described above was repeated using a 65° C. water bath to kill $^{14}$C-labeled cells prior to algal-fungal reciprocal pairings. *Mortierella elongata* incorporates a small amount (1.3%) of $^{14}$C-carbon from dead algal cells, compared to $^{14}$C-carbon acquired from living algal cells (12.7%) (FIG. 2C). In contrast, the algal cells attached to fungal hyphae (att) and those free in the medium (free) acquired more $^{14}$C-carbon (att, 2.4%; free, 15.8%) from dead fungal cells (FIG. 2D). The total abundance of $^{14}$C-carbon was higher in the free algal cells, because most of the *Nannochloropsis oceanica* cells were free in the medium.

Second, confocal microscopy and Sytox Green staining was used to assess whether fungal and algal cells remained alive during co-culture. These results confirmed that most algal and fungal cells remain alive throughout the co-cultivation of $^{14}$C-labeling experiment and also demonstrate that the heat treatment was effective in killing algal and fungal cells (data not shown). Together these data indicate that carbon-transfer from the algae to the fungus is dependent upon an intimate physical interaction between living partners. In contrast, algae are able to utilize carbon from the fungus grown in the same culture regardless of whether the hyphae are alive or physically connected.

Example 4: Nitrogen Exchange Between Fungi and Algae

Figure 3G:
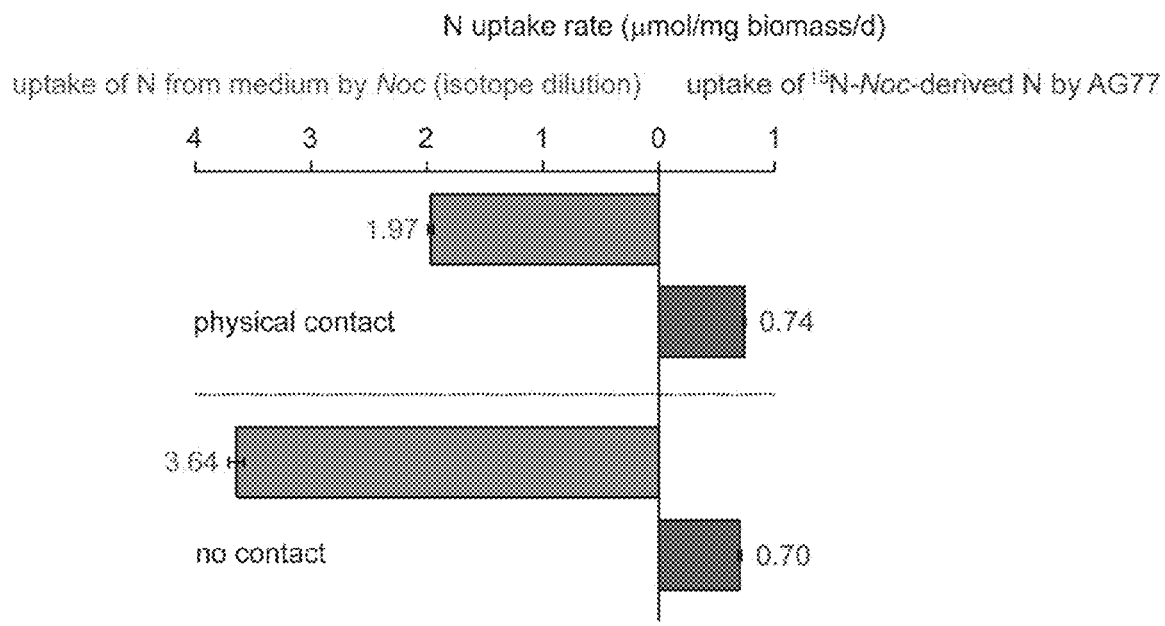
Figure 3H:
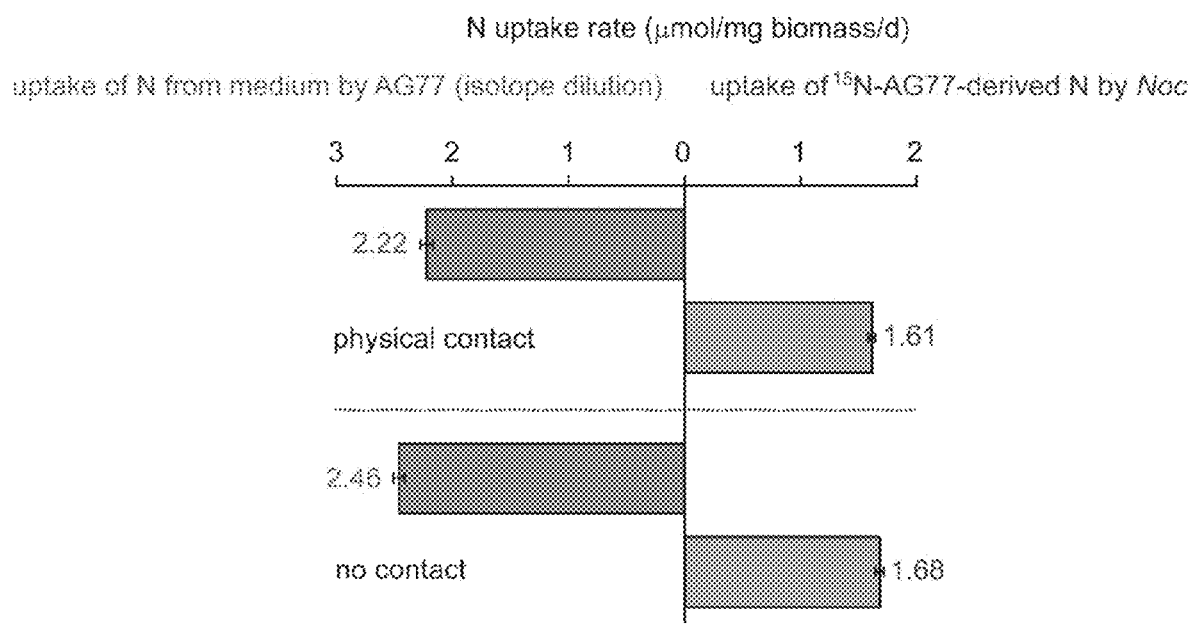

Nitrogen is a major macronutrient that can limit net primary productivity in terrestrial and aquatic ecosystems, including for microalgae such as *N. oceanica*. To determine whether nitrogen-exchange occurs between fungi (*M. elongata*) and algae (*N. oceanica*), the algae were labeled with [$^{15}$N]potassium nitrate and the fungus were labeled with [$^{15}$N]ammonium chloride. The labeled fungal and algal cells were separately co-cultivated with unlabeled partners for one week and then the different cultures were then analyzed for $^{15}$N. Nitrogen ($^{15}$N) transfer occurred between algal and fungal partners, irrespective of whether they were in physical contact or not (FIG. 3A, 3G-3H). Further, over twice as much $^{15}$N (~1.6 μmol/mg biomass/d) was transferred from the $^{15}$N-fungus to the algal recipient, than from the $^{15}$N-algae to the fungus (~0.7 μmol/mg biomass/d—see FIG. 3A, 3G-3H), showing a net nitrogen benefit for the algae when in symbiosis with the fungus.

A nutrient-deficiency test was also performed to assess algae benefits from the nutrient transfer by it fungal partner. Results showed that *N. oceanica* had significantly increased viability when co-cultivated with *M. elongata* under nitrogen or carbon deprivation but not under phosphorus deficient conditions (FIG. 3B-3D). These results indicate that a functional *Mortierella-Nannochloropsis* interaction is established that may be based upon the carbon and nitrogen acquisition and transfer and that is adaptive under nutrient-limited conditions.

Further analysis of the culture supernatant showed an increase in total organic carbon and dissolved nitrogen when the living *Mortierella* fungi were incubated alone in f/2 medium (FIG. 3E-3F) indicative of extracellular release of nutrients by the fungus, and perhaps explaining why physical contact is not required for the $^{14}C$ transfer from the fungus to the algae. It appears that algae benefit from this interaction with *Mortierella* by acquiring both nitrogen and carbon from its fungal symbiont. On the other hand, through an intimate interaction with living photosynthetic algae, *Mortierella* is able to grow in nutrient-limited conditions (PBS buffer) by incorporating algal-derived carbon and nitrogen.

Figure 3I:
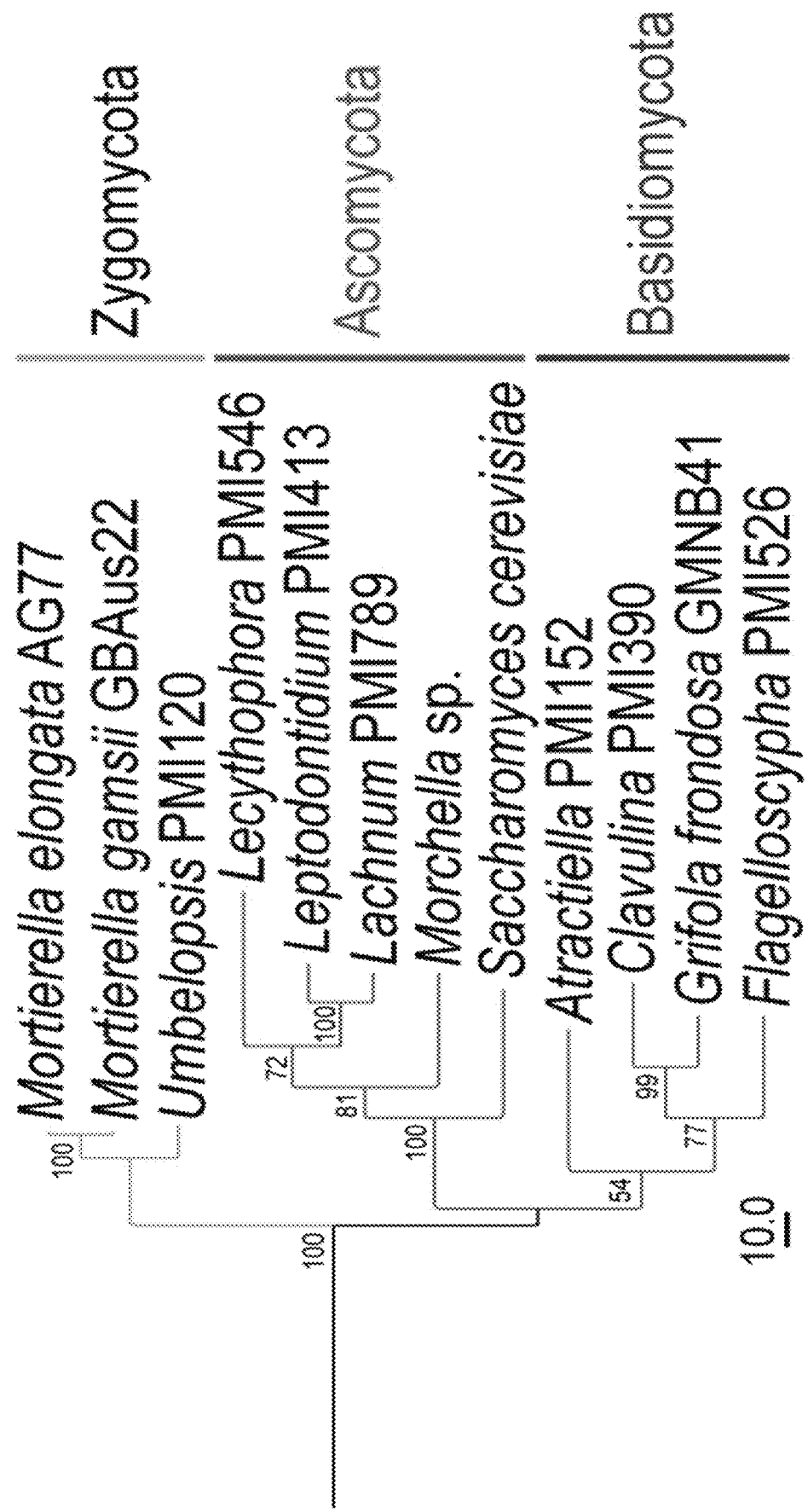
Figure 3J:
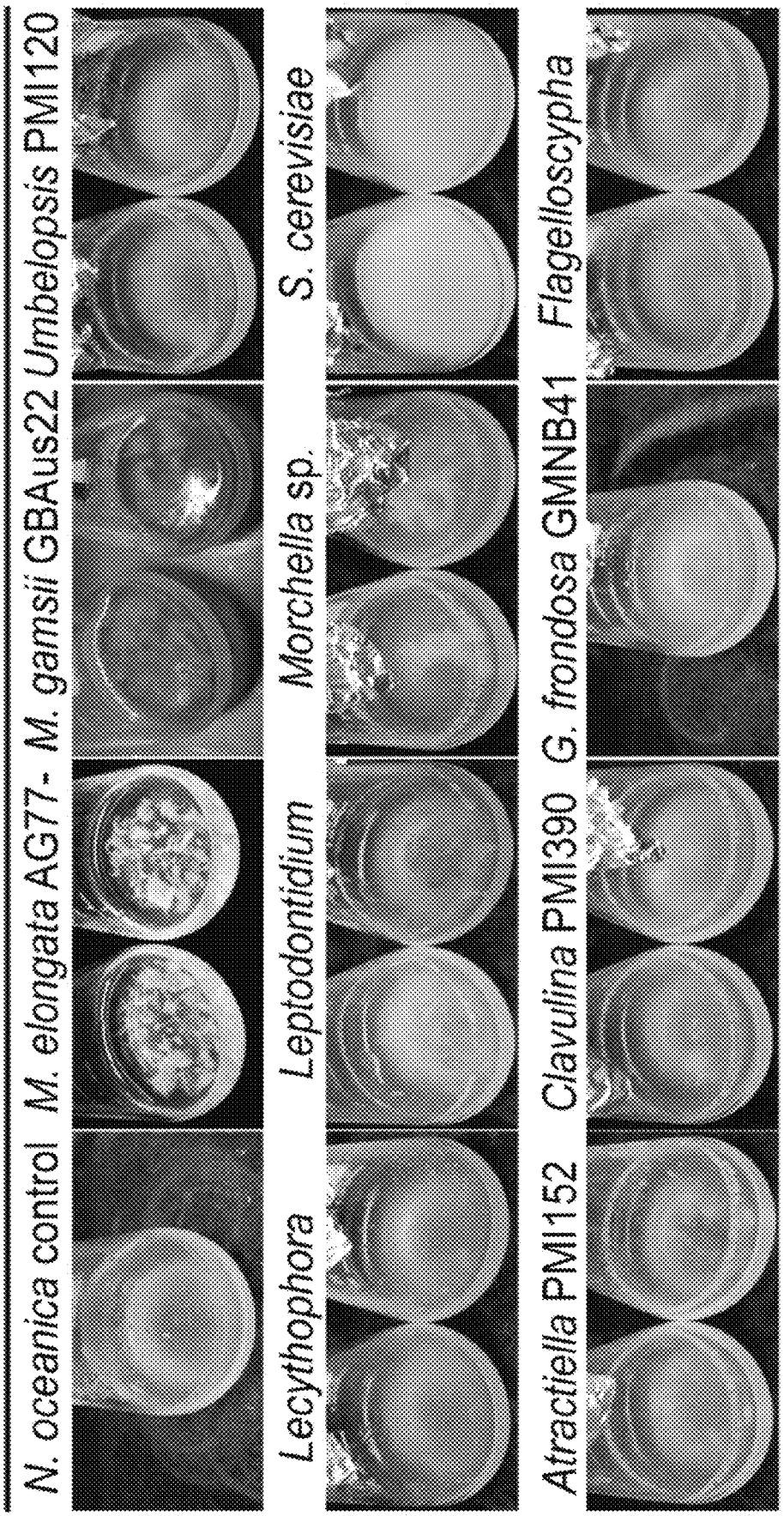

Numerous lineages of fungi have evolved to interact with plants and algae, and the question arises whether the observed interaction is unique to *Mortierella* or alternatively, if it is conserved across diverse lineages of fungi. This was addressed through a series of interaction experiments where *N. oceanica* was paired with a series of fungi sampled across the fungal phylogeny (FIG. 3I-3J). This diverse panel of 21 isolates included the yeast *Saccharomyces cerevisiae*, and filamentous ascomycetes, basidiomycetes, and mucoromycetes isolates representing 3 phyla, 9 orders and 13 families of Fungi. Aside from some *Mortierella* species tested, interactions between these fungi and algae were negative or neutral. *Mortierella elongata* showed the most obvious phenotype and physical attraction to algae, with the algae clustered tightly around the fungal mycelium (FIG. 3J).

Microbial consortia may persist in a stable state, improving the resilience of each to fluctuating environments and stress (Brenner et al., Trends Biotechnol. 26, 483-489 (2008)). To determine whether the observed interactions between *N. oceanica* and *M. elongata* are stable or transient we carried out a series of long-term incubations (from 1 to 6 months) in which the partners were grown together with nutrients refreshed biweekly. After about one month, co-culture confocal microscopy was used to visualize cells inside the thick aggregates that formed between algae and fungus, using the Wheat Germ Agglutinin Conjugate cell wall probe which binds to N-acetylglucosamine, a component in fungal and algal cell walls. From these images some algal cells were within fungal hyphae. Subsequent light and transmission electron microscopies (TEM) were used to provide more details of this interaction and provide evidence for the endosymbiosis of the algae by the fungus. In the algal-fungal aggregates the algae are trapped by the fungus, and some algal cells are indeed intracellular within the hyphae, as shown in TEM micrographs (FIG. 4A-4C). Additional imaging with differential interference contrast (DIC) micrographs and videos demonstrated morphology of the "green hyphae" after different periods of long-term co-culture, further confirming algal endosymbiosis by the fungus and incorporation of intact and functional algal cells intracellularly within the fungal hyphae (FIG. 4D-4H). Both algal and fungal cells remained viable after months of co-culture. This fungal-algae symbiosis may conjure the idea of a lichen, but it differs by the lack of distinct tissue and hyphal structures (i.e. thallus, haustoria) and by the fact that *Mortierella* fungi actually incorporate algal cells intracellularly while lichens do not. The result of this remarkable incorporation of intact and functional algal cells within living fungal mycelia has the hallmarks of a secondary endosymbiosis event.

While observations on endosymbiosis of living eukaryotic cells by fungi have not been reported previously, the rare fungus *Geosiphon pyriformis* (a relative of arbuscular mycorrhizae and of *Mortierella*) is reported to form a unique intracellular association with the cyanobacterium *Nostoc punctiforme* (Mollenhauer et al., Protoplasma. 193, 3-9 (1996)). In this system, the fungus envelops *Nostoc* within a specialized swollen multinucleate fungal "bladder" that is morphologically distinct from the rest of the hyphae. Within this bladder, the cyanobacteria are surrounded by a host-derived symbiosome membrane (Brenner et al., Trends Biotechnol. 26, 483-489 (2008)).

Biogenesis of endosymbiosis of *N. oceanica* by *M. elongata* was evaluated through DIC and time-lapse microscopy. Endosymbiosis was preceded by dense aggregates of algal cells around the fungal hyphal tip (FIG. 4I-1 to FIG. 4I-4). Further, aggregates of algal cells were observed surrounding fungal hyphal tips early in the endosymbiosis process, for example, by 1-2 months. Dense clusters of algal cells formed at the tip of a hypha were consistently observed when the endosymbiosis of algal cells within fungal hyphae happened in plates. Also, hyphae downstream from these tips are often green, and the amount of algae within the cells increased over time (e.g., over 1-2 months). Given these observations we hypothesize that the hyphal tip is the initial point of entry for the algal cells into the fungal protoplasm, as this also where the fungal cell wall is least developed. Not only do algae enter the fungal mycelium, but once inside the mycelium they remain active, appear healthy and are able to multiple. We suspect that the coenocytic nature of *Mortierella*, which has few septa within its mycelium, is one attribute of this fungus that facilities its ability to pack cells with photosynthetic algae. TEM and DIC images show that the fungal host's cell membrane remains intact around the internalized algae (FIG. 4A-4I). Removed from their natural environment, internalized algae would become more completely dependent on the host for nitrogen and other nutrients, which could be exchanged for carbon photosynthate and possibly other metabolites.

Example 5: *N. oceanica* Cell Wall Degradation Upon Interaction with *M. elongata*

*N. oceanica* and *M. elongata* cells were incubated together as described in the previous Examples. Micrographs were taken using scanning electron microscopy (SEM) to view *N. oceanica* cell walls, particularly at the outer layer of the *N. oceanica* cells, after the co-cultivation of *N. oceanica* and *M. elongata* fungi AG77.

A previous study on cell wall structure of *Nannochloropsis gaditana* (Scholz et al., Eukaryot Cell 13(11):1450-64 (2014)) indicates that *Nannochloropsis gaditana* cells have a layer of extensions in their cell wall when observed using high-resolution quick-freeze deep-etch electron microscopy (QFDE-EM). Those studies suggest that there may be a very thin layer of cell wall outside and connected to an extension layer. The thin outer cell wall observed by Scholz et al. (2014) may be fragile because some cells partially lost the thin outer layer during the QFDE-EM.

As illustrated in FIG. 5A-5H, physical interaction between *N. oceanica* and *M. elongata* fungus AG77 led to degradation of the thin outer layer of the *N. oceanica* cell wall, which exposed an extension layer attached to the rugged surface of fungal hypha. This algal extension layer formed irregular-tube-like structures. Such degradation of the *N. oceanica* cell wall was not observed in *N. oceanica* algal cells co-cultivated with *M. elongata* AG77 but separated from the *M. elongata* AG77 fungi by a membrane insert that physically separates the algal and fungal cells but allows metabolic exchange between the two organisms.

These data indicate that physical or intimate interaction is required for the algal cell wall degradation.

REFERENCES

1. R. F. Service, Algae's second try. *Science*. 333, 1238-1239 (2011).
2. N. Okamoto, I. Inouye, A secondary symbiosis in progress? *Science*. 310, 287 (2005).
3. A. F. Little, M. J. H. van Oppen, B. L. Willis, Flexibility in algal endosymbioses shapes growth in reef corals. *Science*. 304, 1492-1494 (2004).
4. E. Tisserant et al., Genome of an arbuscular mycorrhizal fungus provides insight into the oldest plant symbiosis. *Proc. Natl. Acad. Sci. U.S.A.* 110, 20117-20122 (2013).
5. E. F. Y. Hom, A. W. Murray, Plant-fungal ecology. Niche engineering demonstrates a latent capacity for fungal-algal mutualism. *Science*. 345, 94-98 (2014).
6. J. Simon et al., Self-supporting artificial system of the green alga *Chlamydomonas reinhardtii* and the ascomycetous fungus *Alternaria infectoria*. *Symbiosis*, 1-11 (2016).
7. G. Bonito et al., Isolating a functionally relevant guild of fungi from the root microbiome of *Populus*. *Fungal Ecol*. 22, 35-42 (2016).
8. K. Brenner, L. You, F. H. Arnold, Engineering microbial consortia: a new frontier in synthetic biology. *Trends Biotechnol*. 26, 483-489 (2008).
9. D. Mollenhauer, R. Mollenhauer, M. Kluge, Studies on initiation and development of the partner association in *Geosiphon pyriforme* (Kütz.) v. Wettstein, a unique endocytobiotic system of a fungus (Glomales) and the cyanobacterium *Nostoc punctiforme* (Kütz.) Hariot. *Protoplasma*. 193, 3-9 (1996).
10. P. Bonfante, A. Genre, Mechanisms underlying beneficial plant-fungus interactions in mycorrhizal symbiosis. *Nat. Commun*. 1, 48 (2010).
11. P. M. Delaux et al., Algal ancestor of land plants was preadapted for symbiosis. *Proc. Natl. Acad. Sci. U.S.A.* 112, 13390-13395 (2015).
12. K. J. Field et al., Functional analysis of liverworts in dual symbiosis with Glomeromycota and Mucoromycotina fungi under a simulated Palaeozoic $CO_2$ decline. *ISME J*. 10, 1514-1526 (2015).
13. J. W. Spatafora et al., A phylum-level phylogenetic classification of zygomycete fungi based on genome-scale data. *Mycologia*. Resubmitted. Dataset DOI: 10.5281/zenodo.46700 TreeBase: TB2:S18957
14. D. Redecker, R. Kodner, L. E. Graham, Glomalean fungi from the Ordovician. *Science*. 289, 1920-1921 (2000).
15. S. Wodniok et al., Origin of land plants: do conjugating green algae hold the key? *BMC Evol. Biol*. 11, 104 (2011).
16. K. J. Field, S. Pressel, J. G. Duckett, W. R. Rimington, M. I. Bidartondo, Symbiotic options for the conquest of land. *Trends Ecol. Evol*. 30, 477-486 (2015).
17. P. R. Atsatt, Are vascular plants "inside-out" lichens? *Ecology*. 69, 17-23 (1988).
18. A. Vieler et al., Genome, functional gene annotation, and nuclear transformation of the heterokont oleaginous alga *Nannochloropsis oceanica* CCMP1779. *PLoS Genet*. 8, e1003064 (2012).
19. L. P. Partida-Martinez, C. Hertweck, A gene cluster encoding rhizoxin Biosynthesis in *Burkholderia rhizoxina*, the bacterial endosymbiont of the fungus *Rhizopus microsporus*. *Chembiochem*. 8, 41-45 (2007).
20. H. L. Chen, S. S. Li, R. Huang, H. J. Tsai, Conditional production of a functional fish growth hormone in the transgenic line of *Nannochloropsis oculata* (Eustigmatophyceae). *J. Phycol*. 44, 768-776 (2008).
21. A. D. Velichkov, A simple procedure for dissolving fungal cell wall preparations for the analysis of neutral sugars. *World J. Microbiol. Biotechnol*. 8, 527-528 (1992).
22. M. J. Scholz et al., Ultrastructure and composition of the *Nannochloropsis gaditana* cell wall. *Eukaryot. Cell*. 13, 1450-1464 (2014).
23. C. H. Tsai et al., The protein compromised hydrolysis of triacylglycerols 7 (CHT7) acts as a repressor of cellular quiescence in *Chlamydomonas*. *Proc. Natl. Acad. Sci. U.S.A.* 111, 15833-15838 (2014).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:
1. A consortium comprising at least one viable fungus and at least one viable algae linked to or within hyphae of the fungus.
2. The consortium of statement 1, wherein algae is a diatom (bacillariophyte), green algae (chlorophyte), blue-green algae (cyanophyte), golden-brown algae (chrysophyte), haptophyte, or a combination thereof.
3. The consortium of statement 1 or 2, wherein algae is a species of *Amphipleura, Amphora, Aquamortierella, Chaetoceros, Charophyceae, Chlorodendrophyceae, Chlorokybophyceae, Chlorophyceae, Coleochaetophyceae, Cyclotella, Cymbella, Dissophora, Embryophytes, Endogaceae, Fragilaria, Gamsiella, Hantzschia, Klebsormidiophyceae, Lobosporangium, Mamiellophyceae, Mesostigmatophyceae, Modicella, Mortierella, Mucor, Navicula, Nephroselmidophyceae, Nitzschia, Palmophyllales, Prasinococcales, Prasinophytes, Pedinophyceae, Phaeodactylum, Pyramimonadales, Pycnoccaceae, Pythium, Phytophthora, Phytopythium, Rhizopus, Thalassiosira, Trebouxiophyceae, Ulvophyceae, Zygnematophyceae*, or the algae is a combination of species.
4. The consortium of statement 1, 2, or 3, wherein algae is of genera *Ankistrodesmus, Boekelovia, Botryococcus, Chlorella, Chlorococcum, Dunaliella, Isochrysis, Monoraphidium, Nannochloropsis, Oocystis, Oscilla-*

*toria, Pleurochrysis, Scenedesmus, Synechococcus, Tetraselmis,* or a combination thereof.

5. The consortium of statement 1-3, or 4, wherein algae is *Emiliania huxleyi, Gephyrocapsa oceanica, Isochrysis galbana, Isochrysis* sp. T-Iso, *Isochrysis* sp. C-Iso, *Nannochloropsis oceanica,* or a combination thereof.

6. The consortium of statement 1-4, or 5, wherein algae is a photosynthetic algae.

7. The consortium of statement 1-5, or 6, wherein algae may not, in some cases, be *Nostoc punctiforme.*

8. The consortium of statement 1-6, or 7, wherein algae is *Nannochloropsis oceanica* CCMP1779.

9. The consortium of statement 1-7 or 8, wherein the fungus is *Aspergillus, Blakeslea, Botrytis, Candida, Cercospora, Cryptococcus, Cunninghamella, Fusarium (Gibberella), Kluyveromyces, Lipomyces, Morchella, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phqffia), Yarrowia,* or a combination thereof.

10. The consortium of statement 1-8 or 9, wherein the fungus is *Mortierella elongata, Mortierella elongata AG77, Mortierella gamsii, Mortierella gamsii GBAus22, Umbelopsis* sp., *Umbelopsis* PMI120, *Lecythophora* sp., *Lecythophora* PMI546, *Leptodontidium* sp., *Leptodontidium* PMI413, *Lachnum* sp., *Lachnum* PMI789, *Morchella* sp., *Saccharomyces cerevisiae, Atractiella* sp., *Atractiella* PMI152, *Clavulina, Clavulina* PMI390, *Grifola frondosa, Grifola frondosa* GMNB41, *Flagelloscypha* sp., *Flagelloscypha* PMI526, or a combination thereof.

11. The consortium of statement 1-9 or 10, wherein the fungus is *Aspergillus terreus, Aspergillus nidulans, Aspergillus niger, Atractiella* PMI152, *Blakeslea trispora, Botrytis cinerea, Candida japonica, Candida pulcherrima, Candida revkaufi, Candida tropicalis, Candida utilis, Cercospora nicotianae, Clavulina* PMI390, *Cryptococcus curvatus, Cunninghamella echinulata, Cunninghamella elegans, Flagelloscypha* PMI526, *Fusarium fujikuroi (Gibberella zeae), Grifola frondosa* GMNB41, *Kluyveromyces lactis, Lecythophora* PMI546, *Leptodontidium* PM1413, *Lachnum* PM1789, *Lipomyces starkeyi, Lipomyces lipoferus, Mortierella alpina, Mortierella elongata* AG77, *Mortierella gamsii* GBAus22, *Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Umbelopsis* PMI120, *Xanthophyllomyces dendrorhous (Phqffia rhodozyma), Yarrowia lipolytica,* or a combination thereof.

12. The consortium of statement 1-10 or 11, wherein the fungus is not *Geosiphon pyriformis.*

13. The consortium of statement 1-11 or 12, wherein the fungus has more than one algae cell within the fungus hyphae.

14. The consortium of statement 1-12 or 13, wherein the fungus has more than two algae cells within the fungus hyphae.

15. The consortium of statement 1-13 or 14, wherein the fungus has more than five, or more than ten, or more than twenty, or more than twenty five, or more than thirty, or more than forty, or more than fifty, or more than one hundred algae cells within the fungus hyphae.

16. The consortium of statement 1-14 or 15, wherein the fungus has less than 10,000 algae cells within the fungus hyphae, or less than 5000 algae cells within the fungus hyphae, or less than 2000 algae cells within the fungus hyphae, or less than 1000 algae cells within the fungus hyphae.

17. The consortium of statement 1-15 or 16, wherein the algae photosynthetically synthesizes sugars.

18. The consortium of statement 1-16 or 17, wherein the algae has a degraded or missing outer cell wall.

19. The consortium of statement 1-17 or 18, wherein the algae has cell wall extensions.

20. The consortium of statement 1-18 or 19, wherein the algae has cell wall is associated with, bound to, or linked to hyphae of the fungus.

21. A method comprising incubating at least one fungus and at least one algae cell until at least one algae cell is incorporated into hyphae of the fungus, to thereby form a consortium of the at least one fungus and the at least one algae cell.

22. The method of statement 21, wherein at least one fungus and at least one algae cell are incubated together for one or more days, one or more weeks, one or months, one or more years, or indefinitely.

23. The method of statement 21 or 22 wherein at least one fungus and at least one algae cell are incubated at a fungus tissue and algae cell density sufficient for the fungus and the algae come into contact.

24. The method of statement 21, 22, or 23, wherein algae is added to the fungus at a density of about $1 \times 10^4$ algae cells/mL to $1 \times 10^9$ algae cells/mL, or at a density of about $1 \times 10^5$ algae cells/mL to $1 \times 10^8$ algae cells/mL, or at a density of about $1 \times 10^6$ algae cells/mL to $1 \times 10^8$ algae, or at a density of about $1-3 \times 10^7$ cells/mL.

25. The method of statement 21-23 or 24, wherein more fungus tissue by mass than algae cells by mass is incubated together.

26. The method of statement 21-24 or 25, wherein the fungus and the algae cells are incubated at a ratio of from about 10:1 by mass fungal tissue to algal cells, to about 1:1 by mass fungal tissue to algal cells; or from about 5:1 by mass of fungal tissue to algal cells to about 1:1 by mass fungal tissue to algal cells; or at a ratio of about 3:1 by mass fungal tissue to algal cells.

27. The method of statement 21-25 or 26, wherein more algae cells by mass than fungal tissue by mass is incubated.

28. The method of statement 21-26 or 27, wherein the fungus and the algae cells are incubated at a ratio of from about 10:1 by mass algal cells to fungal tissue mass to about 1:1 by mass algal cells to fungal tissue mass; or at a ratio of from about 5:1 by mass algal cells to fungal tissue mass to about 1:1 by mass algal cells to fungal tissue mass.

29. The method of statement 21-27 or 28, wherein one or more fungal species and one or more algae species are incubated in a culture medium that contains some carbohydrate or some sugar.

30. The method of statement 29, wherein the some comprises dextrose, sucrose, glucose, fructose or a combination thereof.

31. The method of statement 29 or 30, wherein the carbohydrate or sugar is present in an amount of about 1 g/liter to about 20 g/liter, or of about 3 g/liter to about 18 g/liter, or of about 5 g/liter to about 15 g/liter.

32. The method of statement 21-30 or 31, wherein one or more fungal species and one or more algae species is incubated in a liquid media, in a semi-solid media, or on a solid media.

33. The method of statement 21-31 or 33, wherein the consortium of the at least one fungus and the at least one algae cell is incubated in a minimal medium.

34. The method of statement 21-32 or 33, wherein the consortium comprising the at least one fungus and the at least one algae cell is incubated or maintained in a minimal medium containing no added carbohydrate or sugar.

35. The method of statement 21-33 or 34, wherein the consortium comprising the at least one fungus and the at least one algae cell grows in a minimal medium containing no added carbohydrate or sugar.

36. The method of statement 21-34 or 35, wherein the consortium synthesizes one or more lipid, carbohydrate, or protein.

37. The method of statement 21-35 or 36, wherein the consortium comprises a lipid content greater than 40%, 50%, 60%, 70%, 80%, or 90% by weight of the consortium.

38. The method of statement 21-36 or 37, wherein after incubating the algae has a degraded or missing outer cell wall.

39. The method of statement 21-37 or 38, wherein after incubating the algae has cell wall extensions.

40. The method of statement 21-38 or 39, wherein after incubating the algae has a cell wall associated with, bound to, or linked to hyphae of the fungus.

41. A consortium comprising *Mortierella elongata* AG77 and *Nannochloropsis oceanica* CCMP1779 within hyphae of the *Mortierella elongata* AG77.

42. A method of generating a consortium between *Mortierella elongata* AG77 and *Nannochloropsis oceanica* CCMP1779, comprising incubating the *Mortierella elongata* AG77 with *Nannochloropsis oceanica* CCMP1779 until the *Nannochloropsis oceanica* CCMP1779 are incorporated within hyphae of the *Mortierella elongata* AG77.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "an algae" or "a fungus" or "a cell" includes a plurality of such algae, fungi, or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A method comprising incorporating at least one *Nannochloropsis* algae cell into hyphae of at least one *Mortierella elongata* fungus by incubating under nutrient deprivation condition at least one *Mortierella elongata* fungus and at least one *Nannochloropsis* algae cell, to thereby form a consortium of the at least one fungus and the at least one algae cell.

2. The method of claim 1, wherein at least one *Mortierella elongata* fungus and at least one *Nannochloropsis* algae cell are incubated together for one or more days, one or more weeks, one or months, one or more years, or indefinitely.

3. The method of claim 1, wherein at least one *Mortierella elongata* fungus and at least one *Nannochloropsis* algae cell are incubated at a density of *Mortierella elongata* fungus cells or tissues, and a *Nannochloropsis* algae cell density sufficient for the fungus and the algae come into contact.

4. The method of claim 1, wherein more *Mortierella elongata* fungus cells or tissues by mass than *Nannochloropsis* algae cells by mass is incubated together.

5. The method of claim 1, wherein more *Nannochloropsis* algae cells by number than *Mortierella elongata* fungal cells or tissue pieces by number is incubated.

6. The method of claim 1, wherein the fungus and the algae cells are incubated at a ratio of from about 10:1 by mass *Nannochloropsis* algal cells to *Mortierella elongata* fungal tissue mass to about 1:1 by mass algal cells to fungal tissue mass.

7. The method of claim 1, wherein one or more *Mortierella elongata* fungal species and one or more *Nannochloropsis* algae species are incubated in a culture medium that contains some carbohydrate or some sugar.

8. The method of claim 7, wherein the carbohydrate or sugar is present in an amount of about 1 g/liter to about 20 g/liter.

9. The method of claim 1, wherein the consortium of the at least one *Mortierella elongata* fungus and the at least one *Nannochloropsis* algae cell is incubated in a minimal medium.

10. The method of claim 1, wherein the consortium synthesizes one or more lipid, carbohydrate, or protein.

11. The method of claim 1, wherein the consortium comprises a lipid content greater than 40% by weight of the consortium.

12. The method of claim 1, comprising incubating a *Mortierella elongata* AG77 fungus with one or more *Nannochloropsis oceanica* CCMP1779 cell until the *Nannochloropsis oceanica* CCMP1779 are incorporated within hyphae of the *Mortierella elongata* AG77.

\* \* \* \* \*

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: A synthetic primer

```
<400> SEQUENCE: 1
agaggagcca tggtaggac                                                   19

<210> SEQ ID NO 2
<211> LENGTH: 17
<212> TYPE: DNA
<213> ORGANISM: Artificial Sequence
<220> FEATURE:
<223> OTHER INFORMATION: A synthetic primer

<400> SEQUENCE: 2
tcgttccacg cgctggg                                                     17

<210> SEQ ID NO 3
<211> LENGTH: 19
<212> TYPE: DNA
<213> ORGANISM: Artificial Sequence
<220> FEATURE:
<223> OTHER INFORMATION: A synthetic primer

<400> SEQUENCE: 3
cttgccaccc ttgccatcg                                                   19

<210> SEQ ID NO 4
<211> LENGTH: 21
<212> TYPE: DNA
<213> ORGANISM: Artificial Sequence
<220> FEATURE:
<223> OTHER INFORMATION: A synthetic primer

<400> SEQUENCE: 4
aacgtcgtcg ttatcggaca c                                                21

<210> SEQ ID NO 5
<211> LENGTH: 19
<212> TYPE: DNA
<213> ORGANISM: Artificial Sequence
<220> FEATURE:
<223> OTHER INFORMATION: A synthetic primer

<400> SEQUENCE: 5
tcacgwcctc ccatggcgt                                                   19

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
aaggagggtc gtcttcgtgg                                                  20
```